is011920184B2

United States Patent
Kokoris et al.

(10) Patent No.: US 11,920,184 B2
(45) Date of Patent: *Mar. 5, 2024

(54) CONCENTRATING A TARGET MOLECULE FOR SENSING BY A NANOPORE

(71) Applicant: Roche Sequencing Solutions, Inc., Pleasanton, CA (US)

(72) Inventors: Mark Stamatios Kokoris, Bothell, WA (US); Robert N. McRuer, Mercer Island, WA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/071,778

(22) Filed: Oct. 15, 2020

(65) Prior Publication Data
US 2022/0307067 A1    Sep. 29, 2022

Related U.S. Application Data

(63) Continuation of application No. 15/585,029, filed on May 2, 2017, now Pat. No. 10,851,405, which is a continuation of application No. 14/075,837, filed on Nov. 8, 2013, now Pat. No. 9,670,526.

(60) Provisional application No. 61/724,821, filed on Nov. 9, 2012.

(51) Int. Cl.
  *C12Q 1/6806*    (2018.01)
  *C12Q 1/6869*    (2018.01)
  *G01N 33/543*    (2006.01)

(52) U.S. Cl.
  CPC ......... *C12Q 1/6806* (2013.01); *C12Q 1/6869* (2013.01); *G01N 33/54373* (2013.01)

(58) Field of Classification Search
  CPC ............... C12Q 1/6806; C12Q 1/6869; C12Q 2563/131; C12Q 2565/531; C12Q 2565/631; G01N 33/54373
  See application file for complete search history.

(56) References Cited

U.S. PATENT DOCUMENTS

| | | | |
|---|---|---|---|
| 6,465,193 B2 | 10/2002 | Akeson et al. | |
| 7,939,259 B2 | 5/2011 | Kokoris et al. | |
| 8,586,301 B2 | 11/2013 | Kokoris et al. | |
| 9,670,526 B2 * | 6/2017 | Kokoris | C12Q 1/6806 |
| 10,851,405 B2 * | 12/2020 | Kokoris | G01N 33/54373 |
| 2011/0136676 A1 | 6/2011 | Greene | |
| 2013/0240359 A1 | 9/2013 | Turner et al. | |
| 2018/0291441 A1 | 10/2018 | Brown et al. | |

FOREIGN PATENT DOCUMENTS

| | | | |
|---|---|---|---|
| WO | 2006028508 A2 | 3/2006 | |
| WO | 2008/157696 A2 | 12/2008 | |
| WO | 2009055617 A1 | 4/2009 | |
| WO | 2010088557 A1 | 8/2010 | |
| WO | 2012/003330 A2 | 1/2012 | |
| WO | 2012/164270 | 12/2012 | |
| WO | WO-2013014451 A1 * | 1/2013 | ........... C12Q 1/6811 |

OTHER PUBLICATIONS

Asghar, W. et al., Solid State Nanopores for Selective Sensing of DNA, Nanopores—Sensing and Fundamental Biological Interactions, 2011, pp. 107-128, Ch. 5, Springer, New York, NY.
Atanasov, et al. Membrane on a chip: a functional tethered lipid bilayer membrane on silicon oxide surfaces.Biophys J. Sep. 2005;89(3):1780-8.
Branton et al., 2008, "The potential and challenges of nanopore sequencing", Nature Biotechnology, 26(10):1146-1153.
Butler et al, 2008, "Single-molecule DNA detection with an engineered MspA protein nanopore", PNAS, 105(52):20647-20652.
Chan, Y-H et al., Effects of linker sequences on vesicle fusion mediated by lipid-anchored DNA oligonucleotides, PNAS, Jan. 27, 2009, pp. 979-984, 106 (4).
Cheley, S. et al., Stochastic Sensing of Nanomolar Inositol 1,4,5-Trisphosphate with an Engineered Pore, Chemistry & Biology, Jul. 2002, pp. 829-838, vol. 9.
U.S. Appl. No. 61/511,436 provisional application specification (pp. 1-44) filed Jul. 25, 2011, the subject matter of which has been incorporated into US 2018/0291441 published on Oct. 11, 2018, pp. 1-67. (Year 2018).
Derrington, et al. Nanopore DNA sequencing with MspA. Proc Natl Acad Sci US A. Sep. 14, 2010;107(37):16060-5. Epub Aug. 26, 2010.
Graneli, A. et al., Organized Arrays of Individual DNA Molecules Tethered to Supported Lipid Bilayers, Langmuir, 2006, pp. 292-299, 22.
Jackman, J. A., et al., Biotechnology Applications of Tethered Lipid Bilayer Membranes, Materials, 2012, pp. 2637-2657, 5.
Jetha et al, Forming an alpha-Hemolysin Nanopore for Single-Molecule Analysis, Methods in Molecular Biology, 2009, pp. 113-127, vol. 544, Humana Press.
Kasianowicz et al, Characterization of individual polynucleotide molecules using a membrane channel, Proceedings of the National Academy of Sciences USA, Nov. 1996, pp. 13770-13773, vol. 93.
Liu, C. et al., Protein Separation by ElectrophoreticElectroosmotic Focusing on Supported Lipid Bilayers, Anal Chem, Oct. 15, 2011, pp. 7876-7880, 83 (20).
Neumann, J. et al., Transport, Separation, and Accumulation of Proteins on Supported Lipid Bilayers, Nano Letters, 2010, pp. 2903-2908, 10 (8).
PubChem data sheet on Hexadecanoic acid, Printed from PubChem. ncbi.nlm.nih.gov/compound/Palmitic-acid, 2019, pp. 1-66 (Year: 2018).

* cited by examiner

Primary Examiner — Narayan K Bhat
(74) Attorney, Agent, or Firm — Kristen K. Walker

(57) ABSTRACT

Methods and related products are disclosed that improve the probability of interaction between a target molecule and a nanopore by capturing the target molecule on a surface comprising the nanopore. The captured target molecule, the nanopore, or both, are able to move relative to each other along the surface. When the leader of the target molecule is in proximity with the nanopore, interaction of the target portion of the target molecule with the nanopore occurs, thereby permitting sensing of the target portion. Confining the target molecule and nanopore in this manner leads to significantly enhanced interaction with the nanopore.

8 Claims, 8 Drawing Sheets

Specification includes a Sequence Listing.

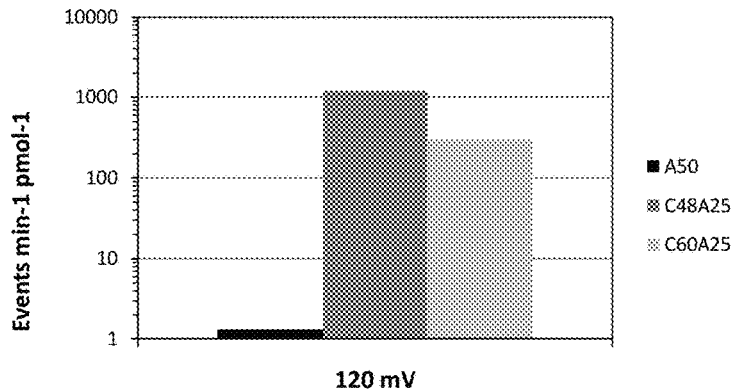
*Figure 4A*
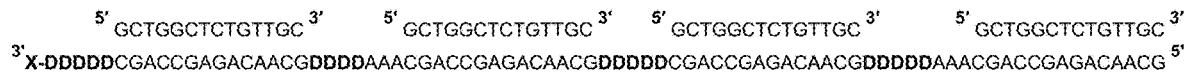
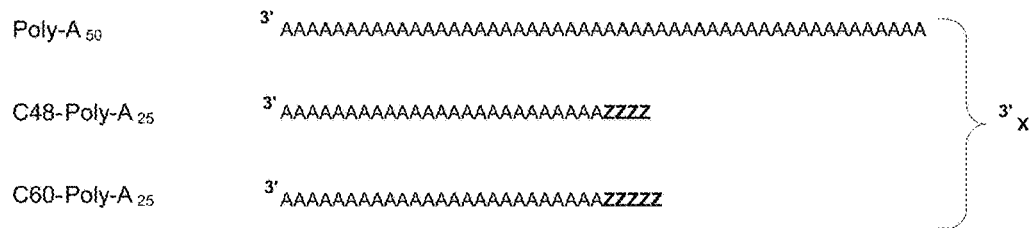
D represents a hexaethyleneglycol phosphodiester (PEG-6)
Z represents a dodecyl phosphodiester (C12)
*Figure 4B*

Control

```
                    3'AGKCKG 5'        3'ATKGKT 5'        3'ATKGKT 5'
   5'
      TGGTTCGTCGAAADDDTCGGGCDAAAAAADDDDTAGCGAXXXXXXXTAGCGAXAAXXXXXX

3'AGKCKG 5'         3'ATKGKT 5'        3'AGKCKG 5'
  TCGGGCXXAAAAAADDDDTAGCGADAAAADDDDTCGGGCDAAAAAADDDDCGACGAACCATCC -Y3'
                                                      for Y3' with dA5C48dA24
```

Target

```
                    3'AGKCKG 5'        3'ATKGKT 5'        3'AGKCKG 5'
   5'
      TGGTTCGTCGAAADDDTCGGGCXXAAAAAADDDDTAGCGAXAAXXXXXXTCGGGCDAAAAAADDDD

3'AGKCKG 5'         3'ATKGKT 5'        3'ATKGKT 5'
  TCGGGCXXAAAAAADDDDTAGCGADAAAADDDDTAGCGAXXXXXXXCGACGAGGGACGGACGGTAGAT-Y3'
```

Symbol Key

$Y^{3'}$:
- $dA_6C_{36}dA_{24}$    AAAAAAZZZAAAAAAAAAAAAAAAAAAAAAAAAA$^{3'}$
- $dA_5C_{48}dA_{24}$    AAAAAZZZZAAAAAAAAAAAAAAAAAAAAAAAAA$^{3'}$
- $dA_4C_{60}dA_{24}$    AAAAZZZZZAAAAAAAAAAAAAAAAAAAAAAAAA$^{3'}$
- $C_{108}dA_{24}$    ZZZZZZZZZAAAAAAAAAAAAAAAAAAAAAAAA $^{3'}$
- $dA_9dA_{24}$    AAAAAAAAAAAAAAAAAAAAAAAAAAAAAAAAA$^{3'}$

D : hexaethyleneglycol phosphodiester (PEG-6)    A : deoxyadenosine
K : G-Clamp    C : deoxycytidine
X : triethyleneglycol phosphodiester (PEG-3)    G : deoxyguanosine
Z : dodecyl phosphodiester (C12)    T : deoxythymidine

*Figure 5*

$Y^{3'}$:
- $dA_5C_{48}dA_{24}L_{25}$    AAAAAZZZZAAAAAAAAAAAAAAAAAAAAAAAAALLLLLLLLLLLLLLLLLLLLLLLLL
- $dA_5C_{48}dA_{24}$    AAAAAZZZZAAAAAAAAAAAAAAAAAAAAAAAAA
- $dA_{11}C_{48}dA_{18}$    AAAAAAAAAAAZZZZAAAAAAAAAAAAAAAAAAAA
- $dA_{18}C_{48}dA_{11}$    AAAAAAAAAAAAAAAAAAZZZZAAAAAAAAAAA where L represents a ethyl phosphodiester

*Figure 6*

Capture Element

CE-1    5' ATCTACCGTCCGTCCC*ZZZZZZZZZZ* 3'

CE-2    5' CCCTGCCTGCC*ZZZZZZZZZZ* 3'

CE-3    5' *ZZZZZZZZZZ*CCGTCCGTCCC 3'

CE-4    5' CCGTCCGTCCCDDDDDD*ZZZZZZZZZZ* 3'

Figure 7

Short ds-DNA Target $C_{48}A_{24}$
```
        3'CCCTCCCTGCCATCTA5'
        5'GGGACGGACGGTAGATAAAAAZZZZAAAAAAAAAAAAAAAAAAAAAAAA 3'
```

$C_{48}L_{24}$
```
        3'CCCTCCCTGCCATCTA5'
        5'GGGACGGACGGTAGATAAAAAZZZZLLLLLLLLLLLLLLLLLLLLLLLL 3'
```

$C_{48}A_{24}L_{100}$
```
        3'CCCTCCCTGCCATCTA5'
        5'GGGACGGACGGTAGATAAAAAZZZZAAAAAAAAAAAAAAAAAAAAAAAALLLLLLLLLLLLLLLL⎞
        →LLLLLLLLLLLLLLLLLLLLLLLLLLLLLLLLLLLLLLLLLLLLLLLLLLLLLLLLLLLLLLLLLL 3'
```

Figure 8

CONCENTRATING A TARGET MOLECULE FOR SENSING BY A NANOPORE

BACKGROUND

Statement Regarding Sequence Listing

The Sequence Listing associated with this application is provided in text format in lieu of a paper copy, and is hereby incorporated by reference into the specification. The name of the text file containing the Sequence Listing is SEQUENCE_LISTING.txt. The text file is 14.3 KB, was created on Oct. 15, 2020, and is being submitted electronically via EFS-Web.

Technical Field

This invention is generally directed to concentrating a target molecule for sensing by a nanopore, as well as methods and products relating to the same.

Description of the Related Art

Measurement of biomolecules is a foundation of modern medicine and is broadly used in medical research, and more specifically in diagnostics and therapy, as well in drug development. Nucleic acids encode the necessary information for living things to function and reproduce, and are essentially a blueprint for life. Determining such blueprints is useful in pure research as well as in applied sciences. In medicine, sequencing can be used for diagnosis and to develop treatments for a variety of pathologies, including cancer, heart disease, autoimmune disorders, multiple sclerosis, and obesity. In industry, sequencing can be used to design improved enzymatic processes or synthetic organisms. In biology, this tool can be used to study the health of ecosystems, for example, and thus have a broad range of utility. Similarly, measurement of proteins and other biomolecules has provided markers and understanding of disease and pathogenic propagation.

An individual's unique DNA sequence provides valuable information concerning their susceptibility to certain diseases. It also provides patients with the opportunity to screen for early detection and/or to receive preventative treatment. Furthermore, given a patient's individual blueprint, clinicians will be able to administer personalized therapy to maximize drug efficacy and/or to minimize the risk of an adverse drug response. Similarly, determining the blueprint of pathogenic organisms can lead to new treatments for infectious diseases and more robust pathogen surveillance. Low cost, whole genome DNA sequencing will provide the foundation for modern medicine. To achieve this goal, sequencing technologies must continue to advance with respect to throughput, accuracy, and read length.

Over the last decade, a multitude of next generation DNA sequencing technologies have become commercially available and have dramatically reduced the cost of sequencing whole genomes. These include sequencing by synthesis ("SBS") platforms (Illumina, Inc., 454 Life Sciences, Ion Torrent, Pacific Biosciences) and analogous ligation based platforms (Complete Genomics, Life Technologies Corporation). A number of other technologies are being developed that utilize a wide variety of sample processing and detection methods. For example, GnuBio, Inc. (Cambridge, MA) uses picoliter reaction vessels to control millions of discreet probe sequencing reactions, whereas Halcyon Molecular (Redwood City, CA) was attempting to develop technology for direct DNA measurement using a transmission electron microscope.

Nanopore based nucleic acid sequencing is a compelling approach that has been widely studied. Kasianowicz et al. (*Proc. Natl. Acad. Sci. USA* 93: 13770-13773, 1996) characterized single-stranded polynucleotides as they were electrically translocated through an alpha hemolysin nanopore embedded in a lipid bilayer. It was demonstrated that during polynucleotide translocation partial blockage of the nanopore aperture could be measured as a decrease in ionic current. Polynucleotide sequencing in nanopores, however, is burdened by having to resolve tightly spaced bases (0.34 nm) with small signal differences immersed in significant background noise. The measurement challenge of single base resolution in a nanopore is made more demanding due to the rapid translocation rates observed for polynucleotides, which are typically on the order of 1 base per microsecond. Translocation speed can be reduced by adjusting run parameters such as voltage, salt composition, pH, temperature, and viscosity, to name a few. However, such adjustments have been unable to reduce translocation speed to a level that allows for single base resolution.

Stratos Genomics has developed a method called Sequencing by Expansion ("SBX") that uses a biochemical process to transcribe the sequence of DNA onto a measurable polymer called an "Xpandomer" (Kokoris et al., U.S. Pat. No. 7,939,259, "High Throughput Nucleic Acid Sequencing by Expansion"). The transcribed sequence is encoded along the Xpandomer backbone in high signal-to-noise reporters that are separated by ~10 nm and are designed for high-signal-to-noise, well-differentiated responses. These differences provide significant performance enhancements in sequence read efficiency and accuracy of Xpandomers relative to native DNA. Xpandomers can enable several next generation DNA sequencing detection technologies and are well suited to nanopore sequencing.

Gundlach et al. (*Proc. Natl. Acad. Sci.* 107(37): 16060-16065, 2010) have demonstrated a method of sequencing DNA that uses a low noise nanopore derived from Mycobacterium smegmatis ("MspA") in conjunction with a process called duplex interrupted sequencing. In short, a double strand duplex is used to temporarily hold the single stranded portion in the MspA constriction. This process enables better statistical sampling of the bases held in the limiting aperture. Under such conditions single base identification was demonstrated; however, this approach requires DNA conversion methods such as those disclosed by Kokoris et al. (supra).

Akeson et al. (WO2006/028508) disclosed methods for characterizing polynucleotides in a nanopore that utilize an adjacently positioned molecular motor to control the translocation rate of the polynucleotide through or adjacent to the nanopore aperture. At this controlled translocation rate (350-2000 Hz (implied measurement rate)), the signal corresponding to the movement of the target polynucleotide with respect to the nanopore aperture can be more closely correlated to the identity of the bases within and proximal to the aperture constriction. Even with molecular motor control of polynucleotide translocation rate through a nanopore, single base measurement resolution is still limited to the dimension and composition of the aperture constriction. As such, in separate work, Bayley et al. (alpha hemolysin: *Chemistry & Biology* 9(7):829-838, 2002) and Gundlach et al. (MspA: *Proceedings of the National Academy of Sciences* 105(52): 20647-20652, 2008) have disclosed methods for engineering nanopores with enhanced noise and base resolution characteristics. However, a demonstration of processive individual nucleotide sequencing has yet to be published that uses either (or both) a molecular motor for translocation control and an engineered nanopore. Current state of the art suggests that signal deconvolution of at least triplet base sets would be required in order to assign single base identity.

Nanopores have proven to be powerful amplifiers, much like their highly exploited predecessors, Coulter Counters. However, a limitation of these devices is their limit of detection. High concentrations of sample materials are required for rapid detection because the ends of long nucleic acid molecules are statistically challenged to find the nanopore entry. Branton et al. (*Nat Biotech* 26(10):1146-1153, 2008) calculated that $10^8$ full genomes would be required to adequately sequence a genome based upon extrapolated throughput. Indeed, improving the limit of detection for many biomolecular measurements is highly desirable for improving sensitivity and extending the range of applications.

While significant advances have been made in this field, there remains a need in the art for new and improved methods and materials for enhancing biomolecular interactions and/or measurements. The present invention fulfills these needs and provides further related advantages.

BRIEF SUMMARY

In brief, a method is disclosed for concentrating a target molecule for nanopore sensing, comprising capturing the target molecule on a surface comprising a nanopore and a hydrophobic domain. The target molecule comprises a target portion, a hydrophobic capture element and a leader for interaction with the nanopore. The hydrophobic capture element of the target molecule is associated with, and capable of movement along, the hydrophobic domain of the surface to bring the leader of the target molecule in proximity with the nanopore. At least the target portion of the target molecule is sensed by the nanopore upon interaction with the nanopore.

In one embodiment, the step of capturing the target molecule on the surface comprises contacting the surface with the target molecule, wherein the target molecule comprises, prior to the contacting step, the target portion, the hydrophobic capture element and the leader.

In another embodiment, the step of capturing the target molecule on the surface comprises linking the hydrophobic capture element associated with the surface to the target portion and leader, thereby capturing the target molecule on the surface.

In a more specific embodiment, the nanopore is a biological nanopore.

In a more specific embodiment, the surface is a lipid bilayer, a solid-state and/or synthetic membrane.

In a more specific embodiment, the target portion comprises nucleic acids, a linear polymer, a molecular bar code and/or an Xpandomer.

In a more specific embodiment, the leader is a hydrophilic polymer.

In a more specific embodiment, the hydrophobic capture element is an aliphatic hydrocarbon.

In a more specific embodiment, the target molecule comprises two or more hydrophobic capture elements.

These and other aspects of the invention will be evident upon references to the attached drawings and following detailed description.

BRIEF DESCRIPTION OF THE SEVERAL VIEWS OF THE DRAWINGS

FIG. 4A illustrates relative event capture in a nanopore due to end modifications of the targeted molecule. FIG. 4B shows a target molecule (SEQ ID NO: 5) that has 4 duplexed regions (SEQ ID NOS: 1-4, respectively) used to pause and measure the molecule in a nanopore. The end-modifications (SEQ ID NOS: 25-27, respectively) ($^{3'}$x) are shown below the target molecule in FIG. 4B.

FIG. 5 illustrates the structure of a control (SEQ ID NO: 6) and a target molecule (SEQ ID NO: 7) used to assess the concentration enhancement caused by different end modifications. Structures of five different end modifications ($Y^{3'}$) (SEQ ID NOS: 8-12, respectively) are shown below the target molecule structure, which have hydrophobic groups of different sizes and a fixed leader length.

FIG. 6 illustrates the structures of four additional end modifications (SEQ ID NOS: 13-16, respectively) that have a fixed hydrophobic group size and leaders of different sizes.

FIG. 7 illustrates the structures of four hydrophobic capture elements (SEQ ID NOS: 17-20, respectively) which are designed to hybridize to the target molecule (rather than part of the covalent structure).

FIG. 8 illustrates structures of three end-adapted ds-DNA targets (SEQ ID NOS: 21-23, respectively) used to compare different leaders (SEQ ID NOS: 24).

DETAILED DESCRIPTION

Figure 1:
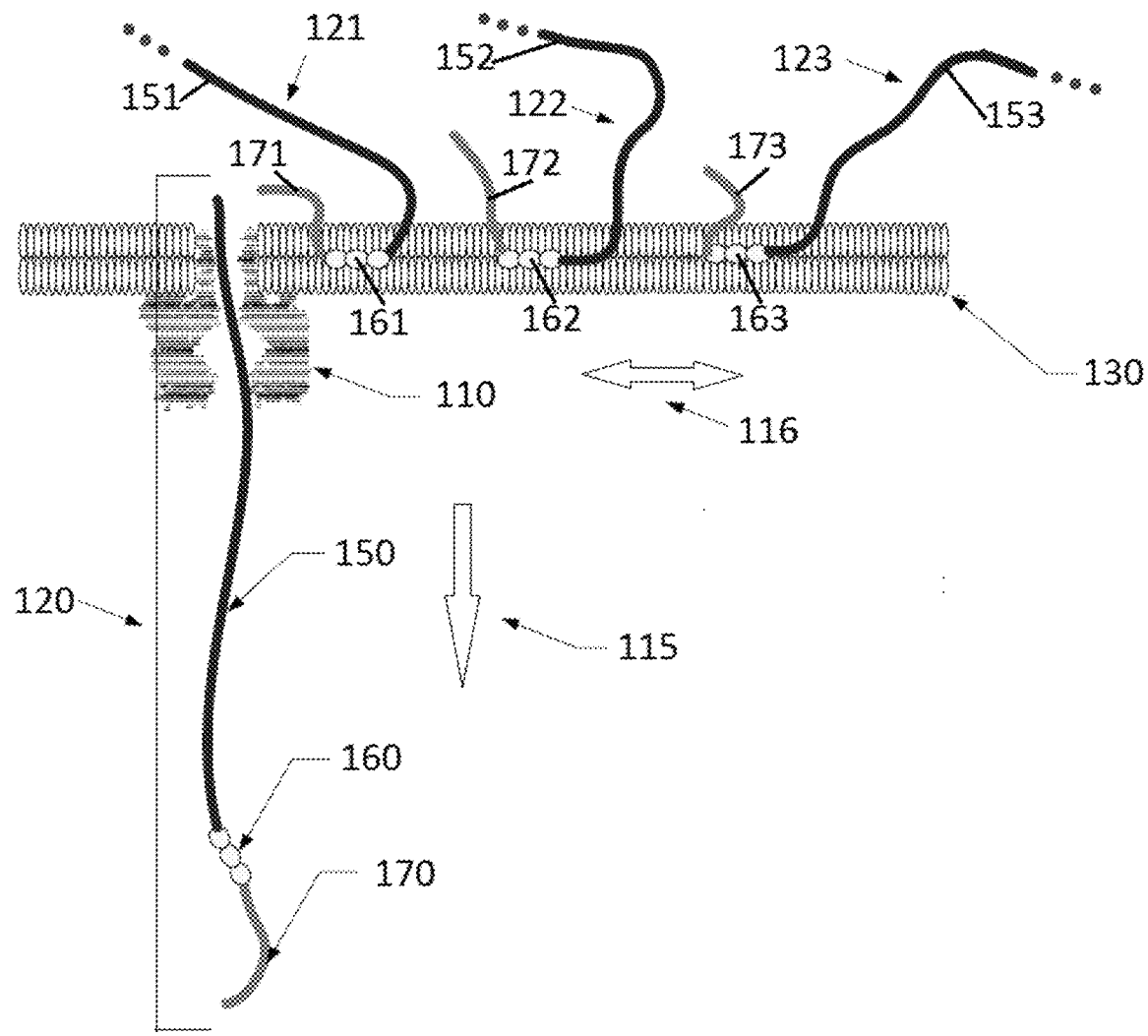
FIG. 1 illustrates capture of several target molecules on a surface comprising a nanopore, as well as translocation of a target molecule through a nanopore.

In brief, the invention improves the probability of interaction between a target molecule and a nanopore by capturing the target molecule on a surface comprising the nanopore. The captured target molecule, the nanopore, or both, are able to move relative to each other along the surface. In this way, the volume occupied by the target molecule and the nanopore is dramatically reduced compared, for example, to a target molecule in a volume of solution that is in contact with the surface. By confining the target molecule and nanopore in this manner—also referred to herein as "concentrating" the target molecule—the probability of interaction between the target molecule and the nanopore is significantly increased. Such increased concentration leads to significantly enhanced translocation of the target molecule, or target portion thereof, through the nanopore.

Nanopores may be broadly classified into two types, biological and synthetic, and both types are intended to be within the scope of this invention. While alpha hemolysin (αHL) is perhaps the most studied biological nanopore to date, this and other over biological nanopores may be utilized in the context of this invention, such as mycobacterium smegmatis porin A (MspA). More recently, synthetic nanopores have been introduced using polymers, glass and thin solid-state membranes. Again, all such design options are within the scope of this invention.

Nanopores are, in effect, small holes through a surface. In the case of biological nanopores, the surface is typically a membrane such as a lipid bilayer. However, other surfaces may also be employed, including lipid monolayers or oil/water interfaces, as well as synthetic and/or inorganic membranes. In the practice of this invention, the surface comprises the nanopore, and also comprises a hydrophobic domain. In the case of a lipid bilayer in aqueous media, for example, the hydrophobic domain is located in the interior portion (i.e., where the hydrophobic tails of the phospholipids lie). In addition to lipid bilayers, other hydrophobic/hydrophilic interfaces can be used for the surface, including (for example) an oil/water interface, a tethered lipid/water interface, an air/water interface, or a lipid-hydrophobic substrate/water interface. In general, these surfaces exhibit differential hydrophobicity and enable capture of the hydrophobic capture element of the target molecule. In addition, such surfaces do not spatially fix the captured target molecule at a given location on the surface, but instead allow the target molecule to diffuse along the surface.

As mentioned above, the target portion may comprise, for example, nucleic acids or a linear polymer. In another embodiment, the target portion may comprise a molecular bar code such as taught in Akeson et al. (U.S. Pat. No. 6,465,193), and/or an Xpandomer such as taught in Kokoris et al. (supra).

The hydrophobic capture element of the target molecule is associated with the hydrophobic domain of the surface. As used herein, associated means that the hydrophobic capture element of the target molecule and the hydrophobic domain of the surface cause the target molecule to remain joined to the surface, while also permitting the captured target molecule to move along the hydrophobic domain of the surface to bring the target molecule in proximity with the nanopore. Such hydrophobic-hydrophobic interaction is mostly an entropic effect associated with disruption of highly dynamic hydrogen bonds between water molecules and nonpolar substances. The strength of hydrophobic interactions depends on temperature, as well as the shape and number of carbon atoms on the hydrophobic compound.

As mentioned above, the target molecule comprises a target portion, a hydrophobic capture element, and a leader. In one embodiment, the surface is contacted with the target molecule such that the capture element of the target molecule is associated with the hydrophobic domain of the surface, thereby capturing the target molecule. In an alternative embodiment, the surface having the hydrophobic capture element associated therewith is contacted with the target portion and leader, thereby capturing the target molecule on the surface.

Once captured by the surface, the leader portion of the target molecule is capable of interacting with the nanopore in a manner that promotes interaction of the target molecule (or target portion thereof) with the nanopore. Such interaction includes, for example, complete or partial translocation through the nanopore. Other interactions may involve positioning a target protein at the nanopore for measurement, or to position a functional protein, such as an enzyme, proximal to the nanopore. Typically, the leader is not hydrophobic, and in one embodiment is a hydrophilic (charged) polymer of low mass to allow interaction with the nanopore when the nanopore and the leader of the target molecule are in close proximity. As mentioned above, the captured target molecule, the nanopore, or both, are capable of movement relative to each other along the surface.

Concentrating the target molecule in this manner increases the number of interactions of the target molecule (or target portion thereof) with the nanopore. As an illustrative example, one application of this invention relates to increasing the number of complete or partial translocations of the target portion, such as DNA/RNA, through a nanopore, wherein the DNA/RNA target portion is combined with a hydrophobic capture element and an oligomer leader. In this representative example, the hydrophobic capture element is captured in the hydrophobic domain of the lipid bilayer that supports the nanopore. However, the target molecule still maintains lateral mobility across the lipid bilayer surface. This increases the probability that the oligomer leader will be drawn into the nanopore and increases the frequency of DNA/RNA translocation through the nanopore.

While nanopores have traditionally been developed for nucleic acid analysis, the target portion of the target molecule may be any of a variety of polymeric materials suitable to measurement and/or detection by the nanopore. In one example, the target portion is an Xpandomer as disclosed in WO2008/157696 (U.S. Pat. No. 7,939,259), as well as related embodiments as disclosed in WO2009/055617, WO2010/088557 and WO2012/003330 (each of which are hereby incorporated by reference in their entirety). For example, Xpandomers synthesized from ligation-based extension of hexamer Xprobes have been end-adapted with C-48-poly$A_{25}$ leaders and have demonstrated translocation rates of 3 events per minute with addition of 10 fmol of material. In this embodiment, the C-48 portion is a concatenate of 4 dodecyl phosphodiester monomers and acts as the hydrophobic capture element, while the poly$A_{25}$ portion is a 25 base deoxyadenosine homopolymer that functions as the leader element. Under identical conditions, the same Xpandomers adapted to poly$A_{25}$ leaders required additions of 1 pmol for the same event rate. In both cases the nanopore was wild-type alpha-hemolysin embedded in a 13 micron diameter lipid bilayer.

In one embodiment, as illustrated in FIG. 1, target molecule 120 comprises target portion 150, hydrophobic capture element 160 and leader 170 which, in this figure, is shown having substantially translocated through nanopore 110 in surface 130. The direction of translocation through the nanopore is shown by arrow 115. In addition to target molecule 120, FIG. 1 also depicts target molecules 121, 122 and 123 having hydrophobic capture elements 161, 162, 163, respectively, captured by the hydrophobic domain of surface 130, which in this figure is depicted as the interior (hydrophobic) portion of a lipid bilayer. Captured target molecules 121, 122 and 123 further comprise target portions 151, 152 and 153 and leaders 171, 172 and 173, respectively. The dots ("• ⊇ 108 ") shown at the ends of target portions 151, 152 and 153 represent additional length of the target portion. Captured target molecules 121, 122 and 123 are capable of movement along surface 130 (as depicted by arrow 116), and such movement brings the leader of a captured target molecule in proximity with the nanopore, as depicted by leader 171 of target molecule 121 being near nanopore 110. Such proximity allows the leader to interact with the nanopore, thus drawing the target molecule into the nanopore for translocation as depicted by target molecule 120.

In a more specific embodiment of FIG. 1, the hydrophobic capture element is a C48 aliphatic hydrophobic group and the leader is poly$A_{24}$ oligomer that acts as a hydrophilic polyanionic leader. The sample reservoir has 1 M potassium chloride in an aqueous 10 mM HEPES pH 7.4 buffer. As the target molecule diffuses through the reservoir, it eventually interacts with the lipid bilayer and the hydrophobic capture element embeds into the hydrophobic portion of the lipid bilayer core. The target molecule is now captured by the surface and the hydrophilic leader is localized in the reservoir close to the surface of the lipid bilayer. Multiple target molecules concentrate on the lipid bilayer in this manner and diffuse along the surface until the leader of the target molecule is proximal to the nanopore. An electric field acting across the pore applies a force on the negatively charged leader, drawing it through the pore and pulling the hydrophobic capture element free of the lipid so translocation of the remainder of the target molecule can proceed. In this manner, the rate of capture and translocation is increased by orders of magnitude relative to the corresponding target portion in solution interacting with the nanopore.

Figure 2:
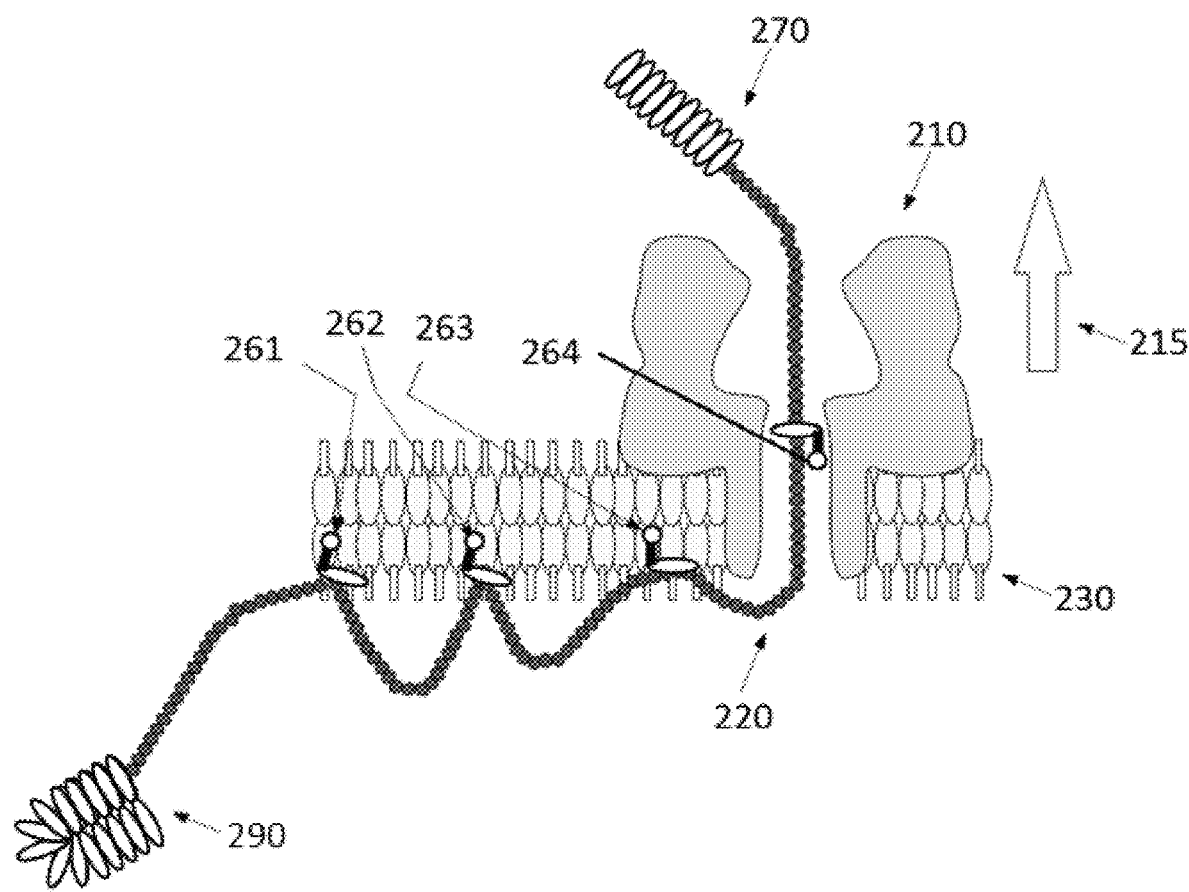
FIG. 2 illustrates translocation of a target molecule through a nanopore, wherein the target molecule has multiple hydrophobic capture elements.

In another embodiment, as illustrated in FIG. 2, the target molecule comprises more than one hydrophobic capture element. In particular, FIG. 2 illustrates a target molecule having four hydrophobic capture elements 261, 262, 263 and 264. Hydrophobic capture elements 261, 262 and 263 are shown as captured by the hydrophobic domain of surface 230, which in FIG. 2 is depicted as a lipid bilayer. Target molecule 220 is shown in FIG. 2 as having partially translocated through nanopore 210 in the direction of arrow 215. Hydrophobic capture element 264 is depicted as having already been dislodged from the hydrophobic domain of surface 230, and is in the process of translocating through the nanopore.

In a more specific embodiment of FIG. 2, a control molecule was prepared having six ligated heterogeneous polymer units, with each polymer unit having four PEG-6 (hexaethyleneglycol phosphodiester) with an amino-modified base. One end of the polymer was adapted with a poly-$A_{50}$ oligomer (forming the leader) (270). The structure on the other end of the polymer is a hairpin loop (290) that is used to prevent backward entry into the pore. The hairpin loop is too large to enter the pore first, but when the hairpin loop is pulled through at the end, the duplex portion will open and unfold the loop, allowing it to translocate. This control molecule was compared to a target molecule which is identical except that each pendant amino group (of the amino-modified base) was conjugated with a DiBenzoCycloOctyl (DBCO) hydrophobic moiety (forming the hydrophobic capture element). For the resulting target molecule, the DBCO moieties interact with the hydrophobic interior of the lipid bilayer, thus capturing the target molecule on the surface, and thereby increasing the concentration of the leader (the poly-$A_{50}$ segment) near the nanopore. Having the leader in close proximity with the nanopore increases the probability that the target molecule will be translocated through the nanopore.

Translocation frequency through the nanopore (alpha hemolysin) of the target molecule compared to the control molecule showed increases of 30, 15, 9, 10 and 8 times for applied potentials of 100, 110, 120, 130 and 140 mV, respectively. For these measurements, the cis and trans reservoirs had 2.0 M LiCl, 10 mM HEPES, pH of 7.4 at a temperature of 10° C. and 15 pmol of control or target molecule was added to the 100 μl cis reservoir. The nanopore was a wild-type α-hemolysin (Sigma Aldrich) and the lipid bilayer was formed on a 13 micron diameter teflon aperture with 1,2-diphytanoyl-sn-glycero-3-phosphoethanolamine (Avanti Polar Lipids) lipid bilayer. (Such methods follow those described by Jetha et al., Chapter 9. *Micro and Nano Technologies in Bioanalysis*, Humana Press 2009, which is incorporated herein by reference.)

In FIGS. 1 and 2 discussed above, capturing the target molecule on the surface comprises contacting the surface with the target molecule, wherein the target molecule comprises the target portion, the hydrophobic capture element and the leader prior to the capturing step. In another embodiment, capturing the target molecule on the surface comprises contacting the surface with the hydrophobic capture element and linking the hydrophobic capture element to the target portion and leader to yield the captured target molecule on the surface.

Figure 3:
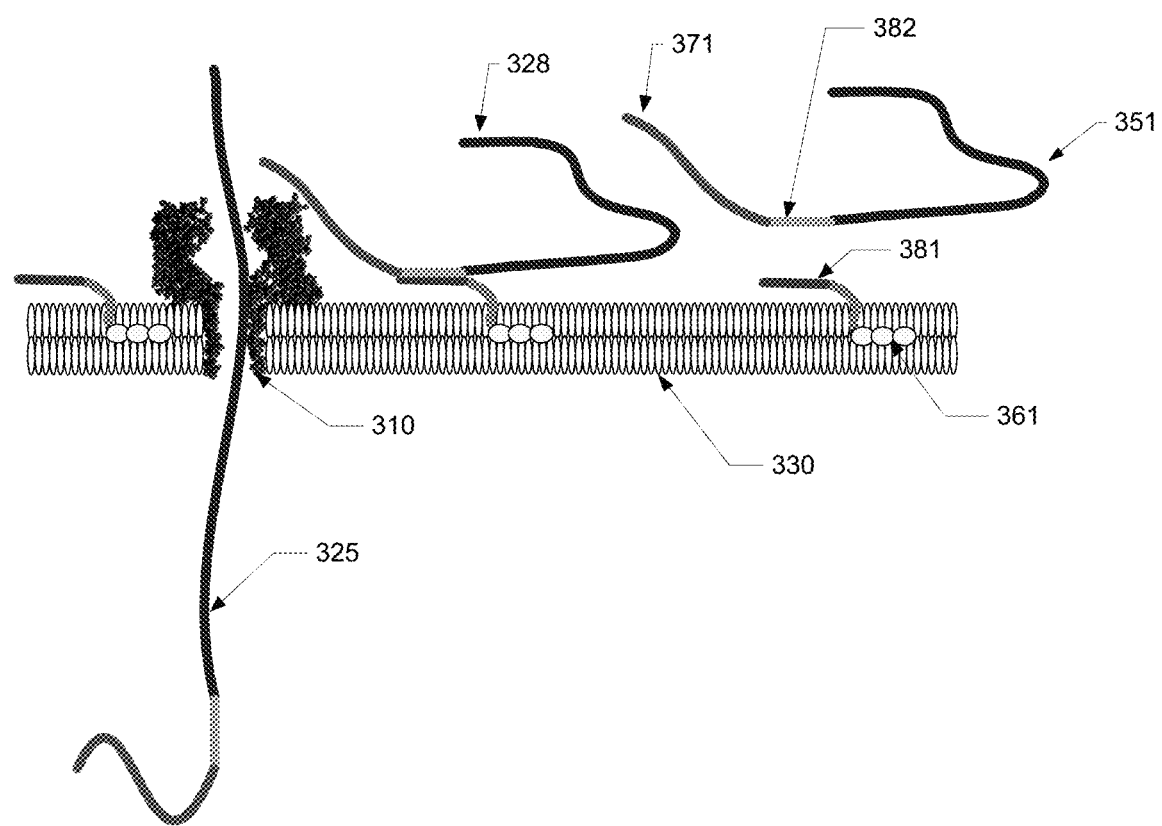
FIG. 3 illustrates linking the leader and target portion of the target molecule to the hydrophobic capture element on a surface, as well as translocation of the leader and target portion of the target molecule (but not the hydrophobic capture element) through a nanopore.

Accordingly, and in another embodiment as illustrated in FIG. 3, hydrophobic capture element 361 is captured by the hydrophobic domain of surface 330, which in this figure is depicted as a lipid bilayer. The hydrophobic element 361 may be captured during the formation of surface 330 or may be captured after surface 330 is formed. Hydrophobic capture element 361 further comprises linking element 381 which permits linkage of hydrophobic capture element 361 to leader 371 and target portion 351 by attachment to corresponding linking element 382. Upon linkage of the capture element to the leader and target portion, target molecule 328 is both formed and captured on the surface. Once captured, the target molecule is capable of diffusing along the surface until the leader of the target molecule is proximal to nanopore 310, as depicted by target molecule 328 in FIG. 3. Such proximity allows the leader to interact with the nanopore, thus drawing the leader and target portion of the target molecule (shown as leader/target portion 325) into the nanopore for translocation there through.

In a more specific embodiment of FIG. 3, capture element 361 comprises an aliphatic group and an oligodeoxynucleotide (ODN) linker. The aliphatic group (the hydrophobic capture element) remains embedded within the hydrophobic domain of surface 330, which is shown as a lipid bilayer, and the ODN linker extends out of the lipid bilayer and into the aqueous. In this embodiment the leader and target portion are adapted with a nucleic acid segment 382 complementary to ODN linker 381. This linker pair is used to join (by hybridization) the leader and target portion to the hydrophobic capture element, thereby forming the target molecule at the surface, as depicted by target molecule 328. The aliphatic group (hydrophobic capture element) diffuses freely throughout the plane of the lipid bilayer. This localization to the plane of the lipid bilayer increases the probability of interaction between the captured target molecule and the nanopore, resulting in the leader being electrophoretically drawn into the nanopore. During translocation, either the linker releases (e.g., the hybridized linkage unzips), or the linker remains attached and the hydrophobic capture element is pulled free of the lipid bilayer and is stripped off at the nanopore.

A representative example of such a hydrophobic capture element is disclosed by Chan et al. (*Proceedings of the National Academy of Sciences* 106(4): 979-984, 2009), which discloses the synthesis of a hydrophobic capture element inserted into a lipid bilayer and linked to a vesicle. In this case, the hydrophobic portion of the capture element was one of the lipid molecules that forms the lipid bilayer, and this lipid molecule was conjugated to an ODN linker. The ODN linker, in turn, was used to hybridize to a complement ODN that was conjugated to a vesicle, demonstrating capture of the vesicle. In another example, Grenali et al. (*Langmuir* 22(1):292-299, 2006) showed that bilayers where 0.5% of the lipids were head-adapted with biotin followed by neutravidin would capture biotinylated oligonucleotides. These captured oligonucleotides would freely diffuse along the bilayer surface with a diffusion constant 26% of that for the lipids themselves.

The hydrophobic capture element may be controlled in size to facilitate diffusive capture of the target molecule with limited diffusive release from the surface, such as a lipid bilayer. However, it should also release with sufficient ease and be sized such that translocation is not interrupted. In one embodiment, a single length of an aliphatic element that is in-line with the backbone of the target molecule may be utilized. If the length of the aliphatic element is too short, the hydrophilic portions of the target molecule (such as the leader) will limit its interaction with the lipid bilayer's hydrophobic core. Thus, the hydrophobic capture element should be large enough to resist the entropic force that the target molecule will exert. However, if the hydrophobic capture element is too long, translocation may be limited due to reduced target molecule mobility in the lipid bilayer; namely, the electrophoretic force required to promote translocation could exceed optimum run conditions and reduce measurement quality. In addition, excessively long hydrophobic segments may cause target handling issues (particularly in an aqueous environment) and have a disruptive effect on lipid bilayer stability. To increase the capture strength of the hydrophobic capture element while maintaining shorter lengths, the target molecule may contain additional (i.e., more than one) hydrophobic capture elements. Also, embodiments other than linear in-line geometries may be utilized, such as hydrophobic capture elements pendent or branched off the target molecule backbone.

In a further embodiment, the hydrophobic capture element may be modified in order to selectively pause translocation through the nanopore, as illustrated by the data presented in the bar graph of FIG. 4A. In this experiment, translocation frequencies were measured for the linear polymer of FIG. 4B with 4 nucleic acid duplexes having total contour length of ~45 nm (i.e., the target portion). Using the translocation control method described by Akeson et al. (supra) and Gundlach et al. (supra), the duplexes are used to pause the polymer translocation for a period of time sufficient to measure a distinct current blockage level. The blockage level is determined principally by the duplex at the nanopore entrance and the portion of polymer that threads the nanopore barrel. After a stochastic pause, the duplexes are stripped off the polymer backbone and the polymer translocation proceeds until it is paused by the next duplex portion. This polymer uses the same 14 base-pair duplex but alternates with threaded portions DDDDAAA or DDDDD, where "D" represents a hexaethyleneglycol phosphodiester linked monomer and "A" is an adenosine deoxynucleotide. Translocation of the molecule can be determined from a characteristic signature of 4 levels alternating between current blockage of 0.31 and 0.18 (relative to open pore current). Measurement was made at 20° C., 120 mV, and 1M KCl/10 mM HEPES/pH7.4 buffer. The nanopore was a wild-type α-hemolysin (Sigma Aldrich) and the lipid bilayer was formed on a 13 micron diameter teflon aperture with 1,2-diphytanoyl-sn-glycero-3-phosphoethanolamine (Avanti Polar Lipids) lipid bilayer. The methods follow those described by Jetha et al. (Chapter 9. *Micro and Nano Technologies in Bioanalysis*, Humana Press 2009).

The 3' end of the target portion was linked to one of three groups: (1) polyA$_{50}$ (SEQ ID NO: 25); (2) C48-polyA$_{25}$ (SEQ ID NO: 26) or (3) C60-polyA$_{25}$ (SEQ ID NO: 27). C48 and C60 are carbon chains of 48 and 60 carbons, respectively, synthesized from dodecyl phosphodiester linked monomers. For example, 5 of the 12-carbon monomers may be linked to form a C60 (the phosphate linkage between such C12 monomers is anionic and will moderate the hydrophobicity of the C12 concatenate to some degree). For polymer (1), polyA$_{50}$ (SEQ ID NO: 25) served as the leader to the target portion (without hydrophobic capture element). For polymers (2) and (3), the C48 and C60 segments, respectively, served as the hydrophobic capture elements, while polyA$_{25}$ served as the leader.

Control polymer (1) (i.e., target portion joined to leader without hydrophobic capture element) and target molecules (2) and (3) were measured for translocation frequency through a nanopore. As shown in the bar chart of FIG. 4A, target molecule (2) (C48-polyA$_{25}$) (SEQ ID NO: 26) and (3) (C60-polyA$_{25}$) (SEQ ID NO: 27) had significantly enhanced frequency of translocation events compared to comparative polymer (1) (polyA$_{50}$) (SEQ ID NO: 25). In particular, in relation to the comparative polymer (1), target polymer (2) increased the number of translocation events/min/pmol by 920 times under the same experimental conditions.

It should be noted that the data presented in FIG. 4A were captured on independent runs and the effective measurement time (due to nanopore blockages) varied between runs. Samples were introduced to the 100 microliter Cis reservoir of the nanopore in a 2 microliter aliquot loaded with 15 femtomoles of sample. To maximize translocation rates from the small sample size, the sample was injected directly adjacent to the nanopore, maximizing the sample interaction with the nanopore, but results often varied by factors of 5 or more. Despite these variations, the concentrator method consistently gave higher translocation rates when compared to non-hydrophobic capture sample To reduce sample injection variations, a control molecule was mixed with each target molecule tested. Nanopore translocations of the target and control could be distinguished by their unique sequence of current blockage signals using the duplex translocation control method described above. The results that follow utilize this approach and were derived from measurements made at 20° C. and 130 mV. The Trans well solution used for these measurements was 2M NH4Cl buffered with 10 mM HEPES/pH7.4; the Cis well solution was 0.4M NH4Cl/0.6M Guanidine HCl buffered with 10 mM HEPES/pH7.4. The nanopore was a wild-type α-hemolysin (Sigma Aldrich) and the lipid bilayer was formed on a 13 micron diameter teflon aperture generally using 1,2-diphytanoyl-sn-glycero-3-phosphoethanolamine (Avanti Polar Lipids) lipid bilayer. In all cases duplexes are added to the target or control in excess of the number of binding sites by a factor of 100× and are thermally cycled.

Test molecules were synthesized on a Mermaide 12 oligonucleotide synthesizer (BioAutomation, Texas) using a variety of phosphoamidites listed at the bottom of FIG. 5. In some cases, longer molecules were formed from two parts that are enzymatically ligated to make the full construct. FIG. 5 shows the composition of the target and control molecules. Each had six duplexed regions that provided a different blockage level sequence when measured in the nanopore.

Referring to FIG. 5, two types of 6-base duplexes are shown adjacent to their complementary sites along the target and control molecules (3'AGKCKG5' and 3'ATKGKT5'); each use a modified base-type called a G-Clamp (Glen Research, Sterling, VA, represented as "K") to provide stronger duplexing. This experiment compared translocation rates of the target molecule with five different end-adaptations; namely, dA$_6$C$_{36}$dA$_{24}$ (SEQ ID NO: 8), dA$_5$C$_{48}$dA$_{24}$ (SEQ ID NO: 9), dA$_4$C$_{60}$dA$_{24}$ (SEQ ID NO: 10), C$_{108}$dA$_{24}$ (SEQ ID NO: 11) and dA$_9$dA$_{24}$ (SEQ ID NO: 12). The first four targets had aliphatic segments of different lengths (hydrophobic capture elements) and the latter end-adaptation had no aliphatic segment. In each case the distal dA$_{24}$ was the leader. The control molecule was end-adapted with dA$_5$C$_{48}$dA$_{24}$ (SEQ ID NO: 9), and was mixed at equal concentration with one of the target species. For each measurement, a 2 microliter aliquot containing 150 femtomoles of each was injected adjacent to the nanopore and measured. Translocation events were captured and discriminated to calculate translocation rates for both. The target translocation rate was then normalized with the translocation rate of the control molecule.

Table 1 shows the normalized sample rates of these target molecules after further normalization to the dA$_9$dA$_{24}$ (SEQ ID NO: 12) rate. These are the concentration enhancement factors that indicate the relative increase in sample translocation rates by incorporation of the hydrophobic capture element compared to those without. It is noted that the concentration enhancement factors are less in Table 1 than those shown in FIG. 4A. In this regard, it is believed that the Table 1 data were better controlled for concentration which likely accounts for the discrepancy. However, the data presented in both FIG. 4A and Table 1 illustrate significant enhancement in translocation rates.

TABLE 1

|  | $dA_9dA_{24}$ (SEQ ID NO: 12) | $dA_6C_{36}dA_{24}$ (SEQ ID NO: 8) | $dA_5C_{48}dA_{24}$ (SEQ ID NO: 9) | $dA_4C_{60}dA_{24}$ (SEQ ID NO: 10) | $C_{108}dA_{24}$ (SEQ ID NO: 11) |
|---|---|---|---|---|---|
| Sample Rate (Normalized) | 1 | 30.9 | 28.8 | 26.5 | 12.5 |

The leader length that extends beyond the hydrophobic capture element may also be modified for interaction with the nanopore. To this end, the leader should be of a sufficient length such that its capture in the nanopore exerts enough force to uncouple the target molecule from the bilayer or, depending on the embodiment, unlink the leader/target portion from the hydrophobic capture element. The leader should carry electrostatic charge to promote interaction with the nanopore under an applied electric potential. A nucleic acid is typically anionic and the leader would typically also be anionic. In some cases an end portion of the target portion may also function as the leader. The leader is typically a single linear polymer, but may have two or more linear polymer portions to help improve nanopore interaction, and should also be able to translocate the nanopore so the target molecule can then engage. Leader materials can be synthesized from many anionic, cationic or neutral polymers and may be made of combinations of materials such as (but not limited to) heterogenous or homogeneous polynucleotides, polyethylene glycol, polyvyinyl alcohol, polyphosphates, poly(vinylphosphonate), poly(styrenesulfonate), poly(vinylsulfonate), polyacrylate, abasic deoxyribonucleic acid, abasic ribonucleic acid, polyaspartate, polyglutamate, polyphosphates, and the like. For example, a representative leader may comprise PEG-24 and/or poly-$A_{12}$.

The effect of leader length upon translocation rates was compared by modifying a target with different length leaders that extend beyond the hydrophobic capture element (C48). The same control and target molecules shown in FIG. 5 were used with the end modifications ($Y^{3'}$) shown in FIG. 6. Normalized translocation rate results are shown in Table 2 and are identified as $dA_{18}C_{48}dA_{11}$ (SEQ ID NO: 16), $dA_{11}C_{48}dA_{18}$ (SEQ ID NO: 15), $dA_5C_{48}dA_{24}$ (SEQ ID NO: 14) and $dA_5C_{48}dA_{24}L_{25}$ (SEQ ID NO: 13). All nanopore measurements supporting the results in Tables 1 and 2 used the same experimental conditions and used the same control molecule so they can be directly compared. For this reason, results in both tables are normalized to the $dA_9dA_{24}$ (SEQ ID NO: 12) result of Table 1, thus referencing the enhancement in translocation rate (also referred to as concentration enhancement herein) to a similar molecule with no hydrophobic capture element.

These results indicate that the concentration enhancement factor increases as the polyA leader increases from 11 to 24 bases. In another measurement, using a different target molecule, the influence of end groups $dA_5C_{48}dA_{24}$ (SEQ ID NO: 9) and $dA_5C_{48}dA_{50}$ (SEQ ID NO: 28) were compared. This showed the latter (longer) leader to be 82% of the former indicating the enhancement effect of polyA leaders plateaus in the range of 20 to 50 bases.

The last column of Table 2, shows the enhancement result due to a $dA_{24}$ leader that is extended with a 25 ethyl phosphodiesters ($dA_5C_{48}dA_{24}L_{25}$) (SEQ ID NO: 13). Its concentration enhancement factor was 70% larger than $dA_5C_{48}dA_{24}$ (SEQ ID NO: 14) alone. Additional leader measurements are presented in Table 4.

The hydrophobic capture element is designed to promote mobility in the lipid bilayer and maintain the hydrophobically captured state, but limited enough so that the target can be released when interacting with the nanopore. The element can extend the target backbone and be in-line with the leader or may be pendant to the backbone or may have multiple elements pendant to the backbone. The hydrophobic capture element can be positioned anywhere along the target relative to the leader but can be optimized to improve capture by the nanopore. Materials that comprise the hydrophobic capture element include, but are not limited to, linear and branched aliphatic chains, lipids, fatty acids, DBCO, cholesterol, fluorinated polymers, apolar polymers, steroids, polyaromatic hydrocarbons, hydrophobic peptides, and hydrophobic proteins. This may also include phase transition polymers that can switch from hydrophilic to hydrophobic states under thermal or other environmental change. In some embodiments some or all of the heads of the lipids in a bilayer are reactive and can bind to an adapted target molecule as shown by Grenali et al. (supra). In this case, the lipid is the hydrophobic capture element.

The method variation shown in FIG. 3 was demonstrated using the targets end-adapted with either $dA_9dA_{24}$ (SEQ ID NO: 12) or $dA_5C_{48}dA_{24}$ (SEQ ID NO: 14) and the control shown in FIG. 5. In this example, a hydrophobic capture element was used that has a C120 on one end (synthesized by linking ten, C12 monomers), and an oligomer at the other end. This oligomer was complementary to a nucleic acid region at the end of the target adjacent to the end modification. FIG. 7 shows several different versions of this hydrophobic capture element. For each measurement, a 2 microliter aliquot of 300 femtomoles of a capture element was injected into the cis reservoir adjacent to the nanopore.

TABLE 2

|  | $dA_9dA_{24}$ (SEQ ID NO: 12) | $dA_{18}C_{48}dA_{11}$ (SEQ ID NO: 16) | $dA_{11}C_{48}dA_{18}$ (SEQ ID NO: 15) | $dA_5C_{48}dA_{24}$ (SEQ ID NO: 14) | $dA_5C_{48}dA_{24}L_{25}$ (SEQ ID NO: 13) |
|---|---|---|---|---|---|
| Sample Rate (Normalized) | 1.0 | 2.8 | 10.7 | 28.8 | 49.0 |

The hydrophobic C120 group on the capture element is inserted into the lipid bilayer, with its other oligomer end remaining outside the bilayer in the aqueous buffer. The cis reservoir was then exchanged with fresh buffer and a 2 microliter aliquot of sample was added containing 15 femtomoles of target and 15 femtomoles of control. The target molecule can hybridize to the capture element and diffuse along the plane of the bilayer. In contrast the control shown in FIG. 5 has no complementary region and will not hybridize to the capture elements described in FIG. 7. Nanopore translocation begins when the leader is electrophoretically pulled through and stops at the capture element duplex. The duplex releases due to thermal and electrophoretic pulling forces, allowing translocation to proceed.

Table 3 shows concentration enhancement factors for these molecules (normalized to the target with no hydrophobic capture element; $dA_9dA_{24}$ (SEQ ID NO: 12)). All measurements were made under the same conditions and concentrations described above. Note that molecules adapted with $dA_5C_{48}dA_{24}$ all have a second hydrophobic capture element. Comparing the two CE1 results indicates that having this second hydrophobic capture element increases the concentration enhancement factor. Reducing the duplex length from 16 bases (CE1) (SEQ ID NO: 17) to 11 bases (CE2 (SEQ ID NO: 18), CE3 (SEQ ID NO: 19) and CE4 (SEQ ID NO: 20)), reduces the stability and enhancement is decreased. The CE2 (SEQ ID NO: 18) and CE3 (SEQ ID NO: 19) capture elements had similar structure except the C120 hydrophobic group was positioned on opposite ends of the duplex. CE4 (SEQ ID NO: 20) had 5 PEG-6 spacers between the hydrophobic group and the hybridization site and improved the concentration enhancement relative to both CE2 (SEQ ID NO: 18) and CE3 (SEQ ID NO: 19), which is believe to be due to relaxing how tightly the duplex was held to the lipid bilayer.

TABLE 3

| Capture Element | $dA_9dA_{24}$ (SEQ ID NO: 12) | | $dA_5C_{48}dA_{24}$ (SEQ ID NO: 14) | | | |
|---|---|---|---|---|---|---|
| | None | CE1 | CE1 | CE2 | CE3 | CE4 |
| Sample Rate (Normalized) | 1 | 417 | 890 | 15 | 100 | 298 |

Additional target molecules were tested that were short ds-DNA strands shown in FIG. 8. Unlike the measurements for results in Tables 1, 2 and 3, these targets had only a single duplex and had no control added to them for normalization. Otherwise the measurement conditions were the same. Each was measured with a 30 femtomole sample and all were normalized to $C_{48}A_{24}$ (SEQ ID NO: 21). This indicates that $dL_{24}$ enhances capture by the nanopore more than $dA_{24}$ by a factor of 2.8, and that adding longer extensions of $L_{100}$ provides even greater enhancement.

TABLE 4

| | $C_{48}dA_{24}$ (SEQ ID NO: 21) | $C_{48}L_{24}$ (SEQ ID NO: 22) | $C_{48}dA_{24}L_{100}$ (SEQ ID NO: 23) |
|---|---|---|---|
| Sample Rate (Normalized) | 1.0 | 2.8 | 3.7 |

In addition, the surface can be modified to optimize performance of the hydrophobic capture element. For example, when the surface is a lipid bilayer, increasing mobility of the captured target molecule increases the probability of leader interaction with the nanopore. For example, increasing the area of the lipid bilayer increases the probability that the target molecules will be captured and migrate to the nanopore. Target molecule capture in the bilayer may also be improved by minimizing any undesired trapping on undesired surfaces in the reservoir, such as isolated lipid or non-lipid reservoir walls. The use of tethered bilayers is a powerful design tool that could be used to control the relative mobility and capture kinetics of the bilayer surfaces. Utilizing the characteristics of fixed lipids and lipid additives to define these characteristics, the target molecules can be captured and limited to diffuse in preferred directions along the bilayer surface. For example, by constraining the lipid layer to be a long thin rectangle confines any hydrophobically captured molecules to diffuse principally along its length.

Figure 9:
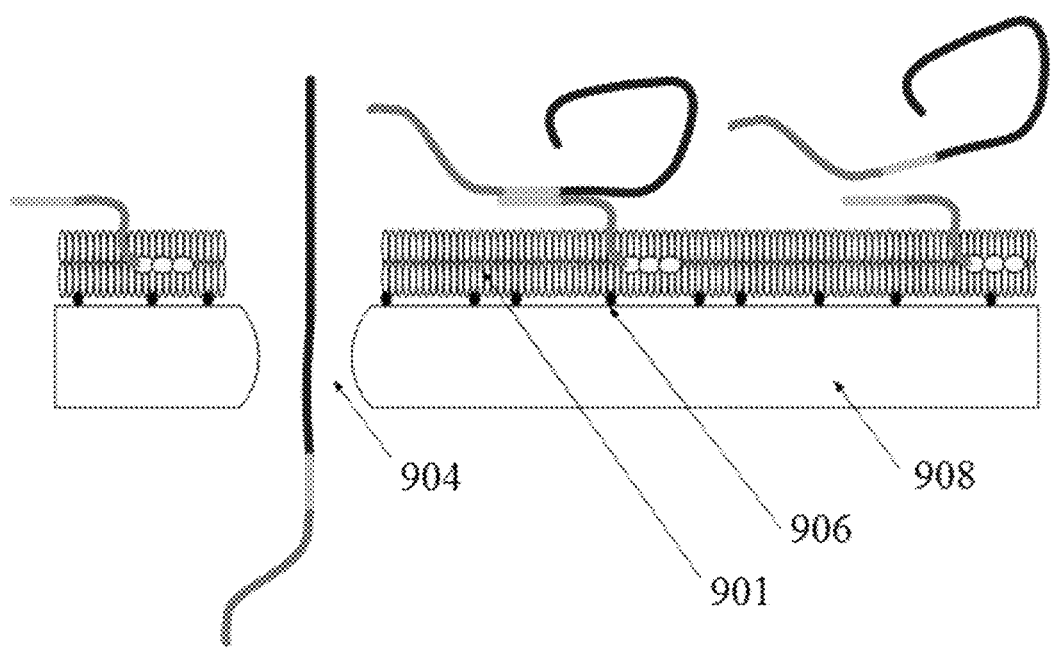
FIG. 9 illustrates concentrating a target molecule utilizing a solid-state nanopore with supported lipid bilayers.

FIG. 9 depicts a supported lipid bilayer (901) used in conjunction with a solid-state nanopore (904). FIG. 9 is similar to the embodiment depicted in FIG. 3, and depicted in this manner (as opposed to the embodiment of FIG. 1 or 2) for purpose of illustration only. Referring to FIG. 9, supported lipid layers are synthesized using a tether species (906) that covalently bond to substrate (908) at one end and imbeds into a bilayer on the other end (see J. Jackman et al., "Biotechnology Applications of Tethered Lipid Bilayer Membranes," Materials 5(12):2637-2657, 2012). A common inorganic film used for solid-state nanopores is silicon nitride which can oxidize to form silicon oxide on its surface. Atanasov et al. has shown supported lipid bilayer formation tether-stabilized with lipids adapted with silanes to bond to a silicon oxide surface ("Membrane on a Chip: A Functional Tethered Lipid Bilayer Membrane on Silicon Oxide Surfaces," *Biophys J.*, 89(3):1780-1788, 2005). These bilayers maintain the required diffusion characteristics that enable the hydrophobically captured molecule to migrate near the nanopore. This bilayer does not need to maintain high electrical impedance, but does require that the bilayer integrity be sufficient near the nanopore such that the target molecule leader can be captured.

Additional forces can be applied to the hydrophobically associated target molecules that will steer them in a preferred direction along the lipid bilayer or other hydrophobic/hydrophilic interface. Graneli et al. ("Organized Arrays of Individual DNA Molecules Tethered to Supported Lipid Bilayers," *Langmuir* 22(1):292-299, 2006) demonstrated that DNA linked to the head group of a lipid that was in a supported lipid bilayer could be moved laterally by the flow of the buffer across the bilayer. Furthermore the DNA-tethered lipid would stop at a defined diffusion barrier, fixing that end of the DNA while the flow remained. After flow was stopped, this lipid molecule and its tethered DNA would diffuse away from the barrier along the bilayer membrane.

Figure 10A:
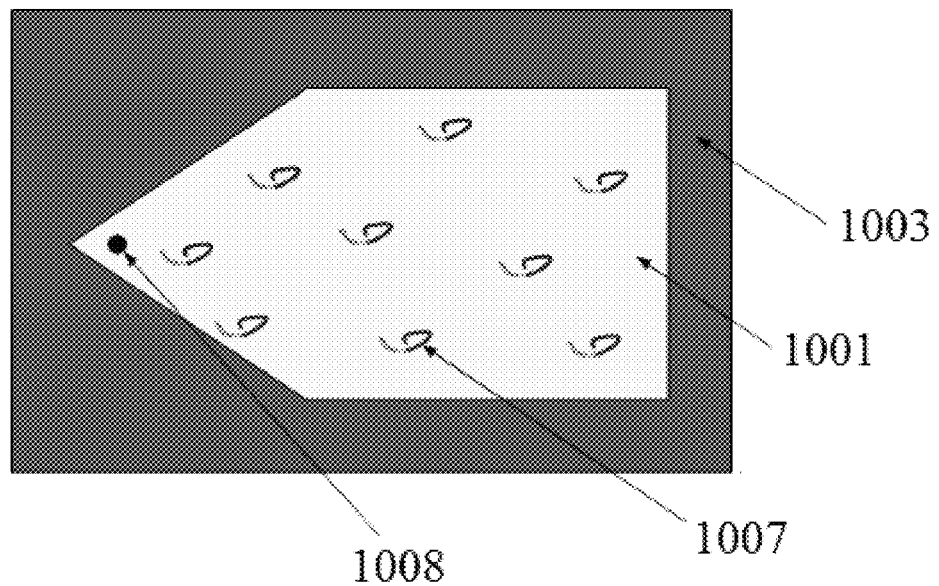
FIG. 10A illustrates the distribution of adapted molecules that are associated with the lipid bilayer and can freely diffuse along the plane of the bilayer.
Figure 10B:
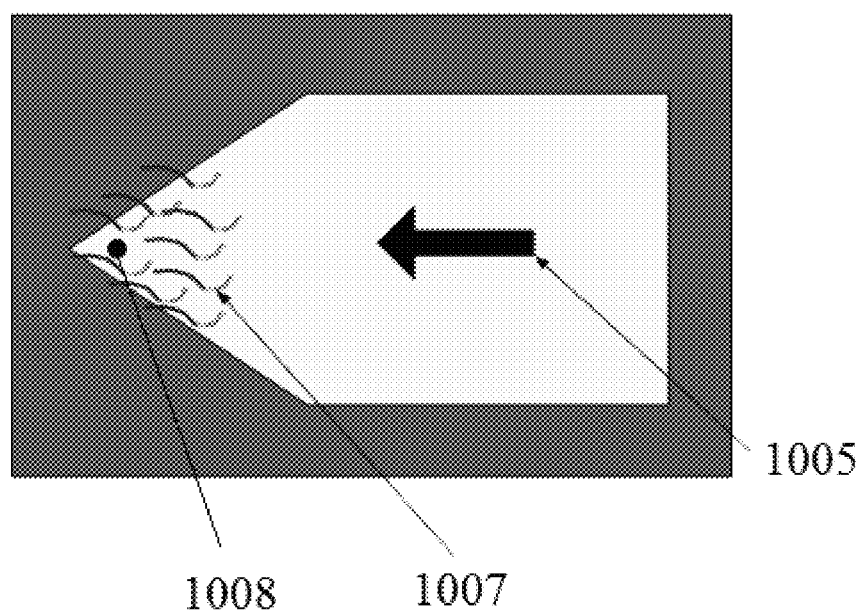
FIG. 10B shows how a shear force, such as flow, can drive such adapted targets to concentrate and localize at a nanopore near the edge of the bilayer plane.

FIGS. 10A and 10B show a supported lipid bilayer (1001) in a shape defined by the diffusion barrier at its edges (1003). Arrow (1005) shows the direction that buffer above the bilayer is flowing. This flowing buffer applies a shear force to the target molecules (1007) that drags them along until they are interrupted by the diffusion barrier (FIG. 10A represents the location of the target molecules before application of the shear force, while FIG. 10B represents location of the target molecules after application of the shear force.) By angling these barriers relative to the flow direction, the target molecules (1007) are concentrated in an area in proximity to nanopore (1008) (see FIG. 10B). This technique can be used to collect and concentrate target molecules in low concentration from larger volumes near a nanopore (or each nanopore in a nanopore array). In addition to flow, other forces can be employed to move the target molecules along the bilayer surface, including electrophoretic/electroosmotic forces (C. Liu et al. "Protein Separation by Electrophoretic-Electroosmotic Focusing on Supported Lipid Bilayers," *Anal. Chem.* 83(20):7876-7880, 2011.), and acoustic forces (J. Neumann et al., "Transport, Separation, and Accumulation of Proteins on Supported Lipid Bilayers," *Nano Lett.* 10(8):2903-2908, 2010).

The method of this invention may be modeled with reservoir target molecule concentration $N_R$ and rate constants for:
i) capture of the leader by the nanopore from the bilayer ($k_{B-trans}$),
ii) capture of the leader by the nanopore from the reservoir ($k_{R-trans}$),
iii) capture of hydrophobic group in the bilayer ($k_{Bcapt}$),
iv) passive release of hydrophobic group from the bilayer ($k_{Brel}$), In this model, the reservoir may be considered infinite and $N_R$ constant. The rate of translocations of molecules pulled directly from the reservoir is:

$$\dot{N}_{R\text{-}trans} = k_{R\text{-}trans} N_R,$$

Along the hydrophobic capture path, the surface concentration of molecules (associated with in the bilayer), $N_B$, changes as:

$$\dot{N}_B = k_{Bcapt} N_R - (k_{Brel} + k_{B\text{-}trans}/A) N_B \text{ when } k_{B\text{-}trans} N_B / A < N_{Bsaturation}$$

Note that this simplified equation has factor of lipid area, A, that is inserted to normalize the rates of molecule capture/release across a lipid area with the molecules translocating thru a single nanopore on the area. This assumes that molecular depletion from the lipid (due to translocation) happens uniformly across A.

At steady-state:

$$0 = k_{Bcapt} N_R - (k_{Brel} + k_{B\text{-}trans}/A) N_B$$

$$N_B = k_{Bcapt} N_R / (k_{Brel} + k_{B\text{-}trans}/A)$$

Choosing area, A, sufficiently large where $A \gg k_{B\text{-}trans}/k_{Brel}$, leads to:

$$N_B = k_{Bcapt} N_R / k_{Brel}$$

A strong hydrophobic group leads to $k_{Bcapt}/k_{Brel} \gg 1$ which leads to high surface concentration of target molecules tethered to the lipid despite relatively low concentration of molecules in the reservoir.

The translocation rates $k_{B-trans}$ and $k_{R-trans}$ are related but differ by the following factors:
i) mobility of target molecule on the lipid surface vs mobility in the reservoir.
ii) effective translocation capture cross-section of molecule end as a function of distance from nanopore. Note that surface tethered case has additional factors to this including position of hydrophobic group and length of the leader.

The rate of translocation can have several regimes including:
i) Diffusion-limited: In this case the molecules must diffuse so their capture end is within range of the nanopore.
ii) End-capture limited: In this case, many molecules are within range (up to the maximum concentration) and translocation rate is limited by the time it takes to capture the end of one of these molecules.
iii) Translocation-limited: In cases where only 1 or some limited number of molecules can enter the nanopore, other molecules can be within range but must wait until the nanopore is available for translocation of another molecule.

Example 1

Nanopore Measurement of Target with C48 Capture Element and PolyA$_{24}$ Oligomer Leader Target molecule synthesis is performed using a Mermaide 4 oligonucleotide synthesizer (BioAutomation, Tex.) using commercially available amidites (Glen Research, Sterling, VA; Chem Genes, Wilmington, MA). The following target molecules are synthesized:

```
Target 1-
                                      (SEQ ID NO: 29)
(dA)24(dCdGdGdGdCdAdAdTdAdA dGdCdCdC);

Target 2-
                                      (SEQ ID NO: 30)
(dA)24 (Dodecyl phosphodiester)4

(SEQ ID NO: 31)
(dA)5 (dCdGdGdGdCdAdA dTdAdAdGdCdCdC);
```

Each target molecule was page purified on a 6% acrylamide TBE-Urea gel (Life Technologies, Carlsbad, CA). Both target molecules contain a poly dA leader portion and a stem-loop structure, which is used to control translocation speed and direction. Target 2 includes the addition of four dodecyl phosphodiester linked monomers, which create the C48 capture element. Each purified target molecule is analyzed using the α-hemolysin nanopore system described by Jetha et al. (Chapter 9. *Micro and Nano Technologies in Bioanalysis*, Humana Press 2009). Targets are added to the cis reservoir of the nanopore device that contains 100 ul 2.0 M LiCl, 10 mM HEPES, pH of 7.4. The trans reservoir contains the same solution. Event frequencies are determined for each target across a range of target inputs (1 fmole to 1 pmole) and voltages (100-140 mVolts) to determine the concentration effect of the C48 capture element.

Example 2

Nanopore Array Capturing Rare Nucleic Acid Targets with Concentrator

Detection and identification of nucleic acids at very low concentration is generally not practical without molecular amplification. By presenting a thin film of sample across a large nanopore sensor array, the target molecules can diffuse to the sensor surface in reasonable time periods. If the sensor surface is primarily a hydrophobic domain, target molecules modified with at least one hydrophobic capture element associate and diffuse along the surface. This greatly increases the likelihood of being sensed.

A microfluid flow cell is designed with a chamber through which electrolyte with sample can pass through. The chamber is 100 microns in height, 3 mm wide and 10 mm long with 1.0 mm diameter input and output ports located at the ends on the top side. On the top side is glass or polymer that is surface treated to inhibit binding to nucleic acids. The bottom side is sealed against a silicon chip that contains a 200×500 array of nanopore cells. The array lies on a grid with 15 micron centers. The outer dimension of the array is 3 mm×7.5 mm and is centered in the chamber. Each cell contains a shallow 10 micron diameter by 3 micron deep well that has an Ag/AgCl electrode at its base. The electrode passes current from contacting electrolyte to be measured by the nanopore cell's transconductance amplifier. The current-converted voltage outputs from the array of nanopore amplifiers are measured at bandwidths exceeding 1 ksample/s/cell.

Across the surface of the silicon chip exposed to the flow chamber, a continuous lipid bilayer is formed in an electrolyte buffer. It is suspended as a membrane over each cell well but is a supported lipid bilayer over the remaining area. Hemolysin nanopores are inserted into the bilayer in a manner to maximize the number of wells with single nanopores. The lipid layer that is connected to the substrate is formed so as to electrically isolate adjacent cell wells from current passing between the substrate and the bilayer. This isolation is sufficient that any leakage currents can be ignored compared to currents that pass through the single nanopore. A characteristic of the continuous bilayer is that molecules adapted with a hydrophobic group as described herein can associate with the bilayer from the flow chamber and will diffuse anywhere along its surface.

A pathogen assay uses hybridization and ligation specificity to identify DNA by using the DNA as a template to hybridize and ligate the target shown in FIG. 5 with $dA_5C_{48}dA_{24}L_{25}$ (SEQ ID NO: 13) as shown in FIG. 6 using methods as taught depicted in U.S. Pat. No. 8,586,301. A 3 microliter sample of this ligation product is injected microfluidically to fill the chamber where the ligation products can diffuse until they contact and associate with the lipid bilayer (due to the $C_{48}$ group). The ligation products then diffuse along the plane of the lipid bilayer until they are captured and measured in a nanopore. This method is highly sensitive because for a 3 microliter sample, all volume diffusing targets are localized to within 100 microns of the active surface, surface-diffusing targets are localized to within 10 microns of a nanopore and measurements provide target specific information from a single molecule.

In alternative embodiments, the geometry described above can be modified in a variety of ways, including (for example) the modifications noted below.
  (i) To inspect larger volumes of sample the chamber and lipid bilayer capture surface can be extended upstream. With suitable diffusion barriers in the lipid, flow induced concentration as described using FIG. 10A and 10B can be used to collect the targets downstream at the nanopore array.
  (ii) Provided the target concentration is uniform in chamber volume, it will collect uniformly at each well. In this case the lipid bilayer need only be continuous over each well. The electrical isolation of each well could coincide with a break in the lipid layer. To maintain high collection efficiency, the area of the bilayers (that collect and along which target molecules can diffuse) should be as large as possible.
  (iii) By adapting the top surface of the flow chamber to have another active silicon chip reduces the average diffusion distance that the injected target must diffuse to reach a bilipid layer and reduces surface area that can lead to sample loss.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Pat. No. 7,939,259, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

---

SEQUENCE LISTING

<160> NUMBER OF SEQ ID NOS: 31

<210> SEQ ID NO 1
<211> LENGTH: 14
<212> TYPE: DNA
<213> ORGANISM: Artificial Sequence
<220> FEATURE:
<223> OTHER INFORMATION: Duplex sequence region used to pause and
      measure molecules

<400> SEQUENCE: 1
gctggctctg ttgc                                                        14

<210> SEQ ID NO 2
<211> LENGTH: 14
<212> TYPE: DNA
<213> ORGANISM: Artificial Sequence
<220> FEATURE:
<223> OTHER INFORMATION: Duplex sequence region used to pause and
      measure molecules

<400> SEQUENCE: 2
gctggctctg ttgc                                                        14

-continued

```
<210> SEQ ID NO 3
<211> LENGTH: 14
<212> TYPE: DNA
<213> ORGANISM: Artificial Sequence
<220> FEATURE:
<223> OTHER INFORMATION: Duplex sequence region used to pause and
      measure molecules

<400> SEQUENCE: 3
gctggctctg ttgc                                                    14

<210> SEQ ID NO 4
<211> LENGTH: 14
<212> TYPE: DNA
<213> ORGANISM: Artificial Sequence
<220> FEATURE:
<223> OTHER INFORMATION: Duplex sequence region used to pause and
      measure molecules

<400> SEQUENCE: 4
gctggctctg ttgc                                                    14

<210> SEQ ID NO 5
<211> LENGTH: 62
<212> TYPE: DNA
<213> ORGANISM: Artificial Sequence
<220> FEATURE:
<223> OTHER INFORMATION: Target DNA molecule
<220> FEATURE:
<221> NAME/KEY: modified_base
<222> LOCATION: (17)...(17)
<223> OTHER INFORMATION: 5 hexaethyleneglycol phosphodiester molecule
      modification
<220> FEATURE:
<221> NAME/KEY: modified_base
<222> LOCATION: (31)...(31)
<223> OTHER INFORMATION: 5 hexaethyleneglycol phosphodiester molecule
      modification
<220> FEATURE:
<221> NAME/KEY: modified_base
<222> LOCATION: (48)...(48)
<223> OTHER INFORMATION: 4 hexaethyleneglycol phosphodiester molecule
      modification
<220> FEATURE:
<221> NAME/KEY: modified_base
<222> LOCATION: (62)...(62)
<223> OTHER INFORMATION: 5 hexaethyleneglycol phosphodiester molecule
      modification

<400> SEQUENCE: 5
gcaacagagc cagcaaagca acagagccag cgcaacagag ccagcaaagc aacagagcca    60
gc                                                                  62

<210> SEQ ID NO 6
<211> LENGTH: 85
<212> TYPE: DNA
<213> ORGANISM: Artificial Sequence
<220> FEATURE:
<223> OTHER INFORMATION: synthetic control molecule used to assess the
      concentration enhancement caused by different end
      modifications
<220> FEATURE:
<221> NAME/KEY: modified_base
<222> LOCATION: (13)...(13)
<223> OTHER INFORMATION: 3 hexaethyleneglycol phosphodiester molecule
      modification
<220> FEATURE:
<221> NAME/KEY: modified_base
<222> LOCATION: (19)...(19)
<223> OTHER INFORMATION: 1 hexaethyleneglycol phosphodiester molecule
      modification
```

```
<220> FEATURE:
<221> NAME/KEY: modified_base
<222> LOCATION: (25)...(25)
<223> OTHER INFORMATION: 4 hexaethyleneglycol phosphodiester molecule
      modification
<220> FEATURE:
<221> NAME/KEY: modified_base
<222> LOCATION: (31)...(31)
<223> OTHER INFORMATION: 7 triethyleneglycol phosphodiester molecule
      modification
<220> FEATURE:
<221> NAME/KEY: modified_base
<222> LOCATION: (37)...(37)
<223> OTHER INFORMATION: 1 triethyleneglycol phosphodiester molecule
      modification
<220> FEATURE:
<221> NAME/KEY: modified_base
<222> LOCATION: (39)...(39)
<223> OTHER INFORMATION: 6 triethyleneglycol phosphodiester molecule
      modification
<220> FEATURE:
<221> NAME/KEY: modified_base
<222> LOCATION: (45)...(45)
<223> OTHER INFORMATION: 2 triethyleneglycol phosphodiester molecule
      modification
<220> FEATURE:
<221> NAME/KEY: modified_base
<222> LOCATION: (50)...(50)
<223> OTHER INFORMATION: 4 hexaethyleneglycol phosphodiester molecule
      modification
<220> FEATURE:
<221> NAME/KEY: modified_base
<222> LOCATION: (56)...(56)
<223> OTHER INFORMATION: 1 hexaethyleneglycol phosphodiester molecule
      modification
<220> FEATURE:
<221> NAME/KEY: modified_base
<222> LOCATION: (60)...(60)
<223> OTHER INFORMATION: 4 hexaethyleneglycol phosphodiester molecule
      modification
<220> FEATURE:
<221> NAME/KEY: modified_base
<222> LOCATION: (66)...(66)
<223> OTHER INFORMATION: 1 hexaethyleneglycol phosphodiester molecule
      modification
<220> FEATURE:
<221> NAME/KEY: modified_base
<222> LOCATION: (72)...(72)
<223> OTHER INFORMATION: 4 hexaethyleneglycol phosphodiester molecule
      modification

<400> SEQUENCE: 6
tggttcgtcg aaatcgggca aaaaatagcg atagcgaaat cgggcaaaaa tagcgaaaaa      60
tcgggcaaaa aacgacgaac catcc                                            85

<210> SEQ ID NO 7
<211> LENGTH: 77
<212> TYPE: DNA
<213> ORGANISM: Artificial Sequence
<220> FEATURE:
<223> OTHER INFORMATION: synthetic target molecule used to assess the
      concentration enhancement caused by different end
      modifications
<220> FEATURE:
<221> NAME/KEY: modified_base
<222> LOCATION: (13)...(13)
<223> OTHER INFORMATION: 3 hexaethyleneglycol phosphodiester molecule
      modification
<220> FEATURE:
<221> NAME/KEY: modified_base
<222> LOCATION: (19)...(19)
<223> OTHER INFORMATION: 2 triethyleneglycol phosphodiester  molecule
      modification
<220> FEATURE:
<221> NAME/KEY: modified_base
<222> LOCATION: (24)...(24)
```

```
<223> OTHER INFORMATION: 4 hexaethyleneglycol phosphodiester molecule
      modification
<220> FEATURE:
<221> NAME/KEY: modified_base
<222> LOCATION: (30)...(30)
<223> OTHER INFORMATION: 1 triethyleneglycol phosphodiester  molecule
      modification
<220> FEATURE:
<221> NAME/KEY: modified_base
<222> LOCATION: (32)...(32)
<223> OTHER INFORMATION: 6 triethyleneglycol phosphodiester  molecule
      modification
<220> FEATURE:
<221> NAME/KEY: modified_base
<222> LOCATION: (38)...(8)
<223> OTHER INFORMATION: 1 hexaethyleneglycol phosphodiester molecule
      modification
<220> FEATURE:
<221> NAME/KEY: modified_base
<222> LOCATION: (44)...(44)
<223> OTHER INFORMATION: 4 hexaethyleneglycol phosphodiester molecule
      modification
<220> FEATURE:
<221> NAME/KEY: modified_base
<222> LOCATION: (50)...(50)
<223> OTHER INFORMATION: 2 triethyleneglycol phosphodiester molecule
      modification
<220> FEATURE:
<221> NAME/KEY: modified_base
<222> LOCATION: (55)...(55)
<223> OTHER INFORMATION: 4 hexaethyleneglycol phosphodiester molecule
      modification
<220> FEATURE:
<221> NAME/KEY: modified_base
<222> LOCATION: (61)...(61)
<223> OTHER INFORMATION: 1 hexaethyleneglycol phosphodiester molecule
      modification
<220> FEATURE:
<221> NAME/KEY: modified_base
<222> LOCATION: (65)...(65)
<223> OTHER INFORMATION: 4 hexaethyleneglycol phosphodiester molecule
      modification
<220> FEATURE:
<221> NAME/KEY: modified_base
<222> LOCATION: (71)...(71)
<223> OTHER INFORMATION: 7 triethyleneglycol phosphodiester molecule
      modification

<400> SEQUENCE: 7
tggttcgtcg aaatcgggca aaaatagcga aatcgggcaa aaaatcgggc aaaaatagcg        60
aaaaatagcg acgacga                                                      77

<210> SEQ ID NO 8
<211> LENGTH: 30
<212> TYPE: DNA
<213> ORGANISM: Artificial Sequence
<220> FEATURE:
<223> OTHER INFORMATION: Synthetic end modification structure
<220> FEATURE:
<221> NAME/KEY: modified_base
<222> LOCATION: (6)...(6)
<223> OTHER INFORMATION: 3 dodecyl phosphodiester molecule modificaton
<220> FEATURE:
<221> NAME/KEY: modified_base
<222> LOCATION: (1)...(30)
<223> OTHER INFORMATION: a = deoxyadenosine

<400> SEQUENCE: 8
aaaaaaaaaa aaaaaaaaaa aaaaaaaaaa                                        30

<210> SEQ ID NO 9
<211> LENGTH: 29
<212> TYPE: DNA
<213> ORGANISM: Artificial Sequence
```

```
<220> FEATURE:
<223> OTHER INFORMATION: Synthetic end modification structure
<220> FEATURE:
<221> NAME/KEY: modified_base
<222> LOCATION: (5)...(5)
<223> OTHER INFORMATION: 4 dodecyl phosphodiester molecule modification
<220> FEATURE:
<221> NAME/KEY: modified_base
<222> LOCATION: (1)...(29)
<223> OTHER INFORMATION: a = deoxyadenosine

<400> SEQUENCE: 9
aaaaaaaaaa aaaaaaaaaa aaaaaaaaa                                   29

<210> SEQ ID NO 10
<211> LENGTH: 28
<212> TYPE: DNA
<213> ORGANISM: Artificial Sequence
<220> FEATURE:
<223> OTHER INFORMATION: Synthetic end modification structure
<220> FEATURE:
<221> NAME/KEY: modified_base
<222> LOCATION: (4)...(4)
<223> OTHER INFORMATION: 5 dodecyl phosphodiester molecule modification
<220> FEATURE:
<221> NAME/KEY: modified_base
<222> LOCATION: (1)...(28)
<223> OTHER INFORMATION: deoxyadenosine

<400> SEQUENCE: 10
aaaaaaaaaa aaaaaaaaaa aaaaaaaa                                    28

<210> SEQ ID NO 11
<211> LENGTH: 24
<212> TYPE: DNA
<213> ORGANISM: Artificial Sequence
<220> FEATURE:
<223> OTHER INFORMATION: Synthetic end modification structure
<220> FEATURE:
<221> NAME/KEY: modified_base
<222> LOCATION: (1)...(24)
<223> OTHER INFORMATION: deoxyadenosine
<220> FEATURE:
<221> NAME/KEY: modified_base
<222> LOCATION: (1)...(1)
<223> OTHER INFORMATION: 9 dodecyl phosphodiester molecule modification

<400> SEQUENCE: 11
aaaaaaaaaa aaaaaaaaaa aaaa                                        24

<210> SEQ ID NO 12
<211> LENGTH: 33
<212> TYPE: DNA
<213> ORGANISM: Artificial Sequence
<220> FEATURE:
<223> OTHER INFORMATION: Synthetic end modification structure
<220> FEATURE:
<221> NAME/KEY: modified_base
<222> LOCATION: (1)...(33)
<223> OTHER INFORMATION: deoxyadenosine

<400> SEQUENCE: 12
aaaaaaaaaa aaaaaaaaaa aaaaaaaaaa aaa                              33

<210> SEQ ID NO 13
<211> LENGTH: 29
<212> TYPE: DNA
<213> ORGANISM: Artificial Sequence
<220> FEATURE:
<223> OTHER INFORMATION: Synthetic end modification structure
<220> FEATURE:
```

```
<221> NAME/KEY: modified_base
<222> LOCATION: (1)...(29)
<223> OTHER INFORMATION: deoxyadenosine
<220> FEATURE:
<221> NAME/KEY: modified_base
<222> LOCATION: (5)...(5)
<223> OTHER INFORMATION: 4 dodecyl phosphodiester molecule modification
<220> FEATURE:
<221> NAME/KEY: modified_base
<222> LOCATION: (29)...(29)
<223> OTHER INFORMATION: 25 ethyl phosphodiester molecule modification

<400> SEQUENCE: 13
aaaaaaaaaa aaaaaaaaaa aaaaaaaaa                                    29

<210> SEQ ID NO 14
<211> LENGTH: 29
<212> TYPE: DNA
<213> ORGANISM: Artificial Sequence
<220> FEATURE:
<223> OTHER INFORMATION: Synthetic end modification structure
<220> FEATURE:
<221> NAME/KEY: modified_base
<222> LOCATION: (1)...(29)
<223> OTHER INFORMATION: deoxyadenosine
<220> FEATURE:
<221> NAME/KEY: modified_base
<222> LOCATION: (5)...(5)
<223> OTHER INFORMATION: 4 dodecyl phosphodiester molecule modification

<400> SEQUENCE: 14
aaaaaaaaaa aaaaaaaaaa aaaaaaaaa                                    29

<210> SEQ ID NO 15
<211> LENGTH: 29
<212> TYPE: DNA
<213> ORGANISM: Artificial Sequence
<220> FEATURE:
<223> OTHER INFORMATION: Synthetic end modification structure
<220> FEATURE:
<221> NAME/KEY: modified_base
<222> LOCATION: (1)...(9)
<223> OTHER INFORMATION: deoxyadenosine
<220> FEATURE:
<221> NAME/KEY: modified_base
<222> LOCATION: (11)...(11)
<223> OTHER INFORMATION: 4 dodecyl phosphodiester molecule modification

<400> SEQUENCE: 15
aaaaaaaaaa aaaaaaaaaa aaaaaaaaa                                    29

<210> SEQ ID NO 16
<211> LENGTH: 29
<212> TYPE: DNA
<213> ORGANISM: Artificial Sequence
<220> FEATURE:
<223> OTHER INFORMATION: Synthetic end modification structure
<220> FEATURE:
<221> NAME/KEY: modified_base
<222> LOCATION: (1)...(29)
<223> OTHER INFORMATION: deoxyadenosine
<220> FEATURE:
<221> NAME/KEY: modified_base
<222> LOCATION: (18)...(18)
<223> OTHER INFORMATION: 4 dodecyl phosphodiester molecule modification

<400> SEQUENCE: 16
aaaaaaaaaa aaaaaaaaaa aaaaaaaaa                                    29

<210> SEQ ID NO 17
<211> LENGTH: 16
```

```
<212> TYPE: DNA
<213> ORGANISM: Artificial Sequence
<220> FEATURE:
<223> OTHER INFORMATION: Synthetic hydrophobic capture element sequence
      which is designed to hybridize to the target
      molecule
<220> FEATURE:
<221> NAME/KEY: modified_base
<222> LOCATION: (16)...(16)
<223> OTHER INFORMATION: 10 dodecyl phosphodiester molecule modification

<400> SEQUENCE: 17
atctaccgtc cgtccc                                                     16

<210> SEQ ID NO 18
<211> LENGTH: 11
<212> TYPE: DNA
<213> ORGANISM: Artificial Sequence
<220> FEATURE:
<223> OTHER INFORMATION: Synthetic hydrophobic capture element sequence
      which is designed to hybridize to the target
      molecule
<220> FEATURE:
<221> NAME/KEY: modified_base
<222> LOCATION: (11)...(11)
<223> OTHER INFORMATION: 10 dodecyl phosphodiester molecule modification

<400> SEQUENCE: 18
ccctgcctgc c                                                          11

<210> SEQ ID NO 19
<211> LENGTH: 11
<212> TYPE: DNA
<213> ORGANISM: Artificial Sequence
<220> FEATURE:
<223> OTHER INFORMATION: Synthetic hydrophobic capture element sequence
      which is designed to hybridize to the target
      molecule
<220> FEATURE:
<221> NAME/KEY: modified_base
<222> LOCATION: (1)...(1)
<223> OTHER INFORMATION: 10 dodecyl phosphodiester molecule modification

<400> SEQUENCE: 19
ccgtccgtcc c                                                          11

<210> SEQ ID NO 20
<211> LENGTH: 11
<212> TYPE: DNA
<213> ORGANISM: Artificial Sequence
<220> FEATURE:
<223> OTHER INFORMATION: Synthetic hydrophobic capture element sequence
      which is designed to hybridize to the target
      molecule
<220> FEATURE:
<221> NAME/KEY: modified_base
<222> LOCATION: (11)...(11)
<223> OTHER INFORMATION: 6 hexaethyleneglycol phosphodiester, 10 dodecyl
      phosphodiester molecule modification.

<400> SEQUENCE: 20
ccgtccgtcc c                                                          11

<210> SEQ ID NO 21
<211> LENGTH: 45
<212> TYPE: DNA
<213> ORGANISM: Artificial Sequence
<220> FEATURE:
<223> OTHER INFORMATION: Synthetic end-adapted ds-DNA target sequence
<220> FEATURE:
<221> NAME/KEY: modified_base
```

```
<222> LOCATION: (21)...(21)
<223> OTHER INFORMATION: 4 dodecyl phosphodiester molecule modification

<400> SEQUENCE: 21
gggacggacg gtagataaaa aaaaaaaaaa aaaaaaaaaa aaaaa                    45

<210> SEQ ID NO 22
<211> LENGTH: 21
<212> TYPE: DNA
<213> ORGANISM: Artificial Sequence
<220> FEATURE:
<223> OTHER INFORMATION: Synthetic end-adapted ds-DNA target sequence
<220> FEATURE:
<221> NAME/KEY: modified_base
<222> LOCATION: (21)...(21)
<223> OTHER INFORMATION: 4 dodecyl phosphodiester, 24 ethyl
      phosphodiester molecule modification

<400> SEQUENCE: 22
gggacggacg gtagataaaa a                                              21

<210> SEQ ID NO 23
<211> LENGTH: 45
<212> TYPE: DNA
<213> ORGANISM: Artificial Sequence
<220> FEATURE:
<223> OTHER INFORMATION: Synthetic end-adapted ds-DNA target sequence
<220> FEATURE:
<221> NAME/KEY: modified_base
<222> LOCATION: (21)...(21)
<223> OTHER INFORMATION: 4 dodecyl phosphodiester molecule modification
<220> FEATURE:
<221> NAME/KEY: modified_base
<222> LOCATION: (45)...(45)
<223> OTHER INFORMATION: 100 ethyl phosphodiester molecule modification

<400> SEQUENCE: 23
gggacggacg gtagataaaa aaaaaaaaaa aaaaaaaaaa aaaaa                    45

<210> SEQ ID NO 24
<211> LENGTH: 16
<212> TYPE: DNA
<213> ORGANISM: Artificial Sequence
<220> FEATURE:
<223> OTHER INFORMATION: Synthetic leader sequence

<400> SEQUENCE: 24
atctaccgtc cctccc                                                    16

<210> SEQ ID NO 25
<211> LENGTH: 50
<212> TYPE: DNA
<213> ORGANISM: Artificial Sequence
<220> FEATURE:
<223> OTHER INFORMATION: Synthetic end modification sequence

<400> SEQUENCE: 25
aaaaaaaaaa aaaaaaaaaa aaaaaaaaaa aaaaaaaaaa aaaaaaaaaa               50

<210> SEQ ID NO 26
<211> LENGTH: 25
<212> TYPE: DNA
<213> ORGANISM: Artificial Sequence
<220> FEATURE:
<223> OTHER INFORMATION: Synthetic end modification sequence
<220> FEATURE:
<221> NAME/KEY: modified_base
<222> LOCATION: (25)...(25)
<223> OTHER INFORMATION: 4 dodecyl phosphodiester molecule modification
```

-continued

```
<400> SEQUENCE: 26
aaaaaaaaaa aaaaaaaaaa aaaaa                                           25

<210> SEQ ID NO 27
<211> LENGTH: 25
<212> TYPE: DNA
<213> ORGANISM: Artificial Sequence
<220> FEATURE:
<223> OTHER INFORMATION: Synthetic end modification sequence
<220> FEATURE:
<221> NAME/KEY: modified_base
<222> LOCATION: (25)...(25)
<223> OTHER INFORMATION: 5 dodecyl phosphodiester molecule modification

<400> SEQUENCE: 27
aaaaaaaaaa aaaaaaaaaa aaaaa                                           25

<210> SEQ ID NO 28
<211> LENGTH: 55
<212> TYPE: DNA
<213> ORGANISM: Artificial Sequence
<220> FEATURE:
<223> OTHER INFORMATION: Synthetic end motification sequence
<220> FEATURE:
<221> NAME/KEY: modified_base
<222> LOCATION: 5
<223> OTHER INFORMATION: 4 dodecyl phosphodiester molecule modification
<220> FEATURE:
<221> NAME/KEY: modified_base
<222> LOCATION: (1)...(55)
<223> OTHER INFORMATION: a = deoxyadenosine

<400> SEQUENCE: 28
aaaaaaaaaa aaaaaaaaaa aaaaaaaaaa aaaaaaaaaa aaaaaaaaaa aaaaa          55

<210> SEQ ID NO 29
<211> LENGTH: 38
<212> TYPE: DNA
<213> ORGANISM: Artificial Sequence
<220> FEATURE:
<223> OTHER INFORMATION: Synthetic target sequence
<220> FEATURE:
<221> NAME/KEY: modified_base
<222> LOCATION: (1)...(38)
<223> OTHER INFORMATION: a = deoxyadenosine
<220> FEATURE:
<221> NAME/KEY: modified_base
<222> LOCATION: (1)...(38)
<223> OTHER INFORMATION: c = deoxycytidine
<220> FEATURE:
<221> NAME/KEY: modified_base
<222> LOCATION: (1)...(38)
<223> OTHER INFORMATION: t = deoxythymidine
<220> FEATURE:
<221> NAME/KEY: modified_base
<222> LOCATION: (1)...(38)
<223> OTHER INFORMATION: g = deoxyguanosine

<400> SEQUENCE: 29
aaaaaaaaaa aaaaaaaaaa aaaacgggca ataagccc                             38

<210> SEQ ID NO 30
<211> LENGTH: 24
<212> TYPE: DNA
<213> ORGANISM: Artificial Sequence
<220> FEATURE:
<223> OTHER INFORMATION: Synthetic target sequence
<220> FEATURE:
<221> NAME/KEY: modified_base
<222> LOCATION: 24
```

```
<223> OTHER INFORMATION: 4 dodecyl phosphodiester molecule modification
<220> FEATURE:
<221> NAME/KEY: modified_base
<222> LOCATION: (1)...(24)
<223> OTHER INFORMATION: a = deoxyadenosine

<400> SEQUENCE: 30
aaaaaaaaaa aaaaaaaaaa aaaa                                        24

<210> SEQ ID NO 31
<211> LENGTH: 19
<212> TYPE: DNA
<213> ORGANISM: Artificial Sequence
<220> FEATURE:
<223> OTHER INFORMATION: Synthetic target sequence
<220> FEATURE:
<221> NAME/KEY: modified_base
<222> LOCATION: (1)...(19)
<223> OTHER INFORMATION: a = deoxyadenosine
<220> FEATURE:
<221> NAME/KEY: modified_base
<222> LOCATION: (1)...(19)
<223> OTHER INFORMATION: c = deoxycytidine
<220> FEATURE:
<221> NAME/KEY: modified_base
<222> LOCATION: (1)...(19)
<223> OTHER INFORMATION: t = deoxythymidine
<220> FEATURE:
<221> NAME/KEY: modified_base
<222> LOCATION: (1)...(19)
<223> OTHER INFORMATION: g = deoxyguanosine

<400> SEQUENCE: 31
aaaaacgggc aataagccc                                              19
```

The invention claimed is:

1. A method for concentrating a target molecule for nanopore sensing, comprising: capturing the target molecule on a surface, wherein the surface comprises a nanopore and a hydrophobic domain, wherein the target molecule comprises a target portion, a hydrophobic capture element and a leader for interaction with the nanopore, wherein the target portion is an Xpandomer, wherein the Xpandomer is a measurable polymer comprising high signal-to-noise reporters that are separated by approximately 10 nm, wherein the hydrophobic capture element is an aliphatic hydrocarbon, wherein the aliphatic hydrocarbon comprises 5 repeats of a 12 carbon monomer, and wherein the leader is a hydrophobic polymer, wherein the hydrophobic polymer comprises 25 repeats of an ethyl phosphodiester, wherein the hydrophobic capture element is associated with, and capable of movement along, the hydrophobic domain of the surface to bring the leader in proximity with the nanopore; and sensing at least the target portion upon interaction with the nanopore.

2. The method of claim 1, wherein the step of capturing the target molecule on the surface comprises contacting the surface with the target molecule, wherein the target molecule comprises, prior to the contacting step, the target portion, the hydrophobic capture element and the leader.

3. The method of claim 1, wherein the step of capturing the target molecule on the surface comprises linking the hydrophobic capture element associated with the surface to the target portion and leader, thereby capturing the target molecule on the surface. nanopore.

4. The method of claim 1, wherein the nanopore is a biological nanopore.

5. The method of claim 1, wherein the surface is a lipid bilayer.

6. The method of claim 1, wherein the surface is a solid-state or synthetic membrane.

7. The method of claim 1, wherein the target portion comprises a molecular bar code.

8. The method of claim 1, wherein the target molecule comprises two or more hydrophobic capture elements.

* * * * *